United States Patent
Cornell et al.

(10) Patent No.: US 10,721,937 B1
(45) Date of Patent: Jul. 28, 2020

(54) PRESERVATIVE SYSTEMS AND COMPOSITIONS AND METHODS INCORPORATING SAME

(71) Applicant: CODEX BEAUTY CORPORATION, Portola Valley, CA (US)

(72) Inventors: Marc Cornell, Portola Valley, CA (US); Barbara A. Paldus, Portola Valley, CA (US)

(73) Assignee: CODEX BEAUTY CORPORATION, Portola Valley, CA (US)

(*) Notice: Subject to any disclaimer, the term of this patent is extended or adjusted under 35 U.S.C. 154(b) by 0 days.

(21) Appl. No.: 16/669,045

(22) Filed: Oct. 30, 2019

Related U.S. Application Data

(60) Provisional application No. 62/845,761, filed on May 9, 2019, provisional application No. 62/861,743, filed on Jun. 14, 2019.

(51) Int. Cl.
| | |
|---|---|
| *A01N 65/40* | (2009.01) |
| *A01N 37/06* | (2006.01) |
| *A01N 31/02* | (2006.01) |
| *A01N 37/40* | (2006.01) |
| *A01N 63/10* | (2020.01) |

(52) U.S. Cl.
CPC ............ *A01N 63/10* (2020.01); *A01N 31/02* (2013.01); *A01N 37/06* (2013.01); *A01N 37/40* (2013.01); *A01N 65/40* (2013.01)

(58) Field of Classification Search
None
See application file for complete search history.

(56) References Cited

U.S. PATENT DOCUMENTS

| | | |
|---|---|---|
| 8,784,910 B2 | 7/2014 | Lutz et al. |
| 9,181,161 B2 | 11/2015 | Rudolph et al. |
| 9,700,507 B1* | 7/2017 | Hakim ............... A61Q 19/007 |
| 10,111,822 B2 | 10/2018 | Shibuya et al. |
| 2006/0210500 A1 | 9/2006 | Bicard-Benhamou et al. |
| 2007/0207113 A1* | 9/2007 | Joerger ............... C11D 3/3418 424/70.31 |
| 2013/0323228 A1 | 12/2013 | Norman |
| 2016/0374352 A1 | 12/2016 | Modak et al. |

FOREIGN PATENT DOCUMENTS

| | | |
|---|---|---|
| KR | 100990765 B1 | 10/2010 |
| KR | 20110139527 A | 12/2011 |
| WO | 2016160309 A1 | 10/2016 |

OTHER PUBLICATIONS

Badcock, "Essential Wholesale & Labs Shares Insight into Natural Preservatives," PRWeb, Jan. 31, 2014, 2 Pages.
Jessop et al., "Opportunities for Greener Alternatives in Chemical Formulations," Green Chemistry, vol. 17, 2015, pp. 2664-2678.
Badcock, "Phenoxyethanol and Skin Deep Ratings," retrieved on May 6, 2019 from https://library.essentialwholesale.com/phenoxyethanol-skin-deep-ratings/ written Jun. 5, 2017, 13 Pages.
Irish, "Are Sodium Benzoate and Phenoxyethanol Safe in Skincare Products?" retrieved on Apr. 30, 2019 from https://www.oznaturals.com/blogs/blog/sodium-benzoate-and-phenoxyethanol written Jul. 10, 2017, 7 Pages.
Jarnot, "Bacteria Hack: Pre- and Probiotics in Skincare," Beauty Heroes, Aug. 13, 2018, 12 Pages.
"Natural Preservatives for Cosmetics," Luisa Fanzani, Mar. 1, 2018, 33 pages. https://luisafanzani.com/natural-preservatives-for-cosmetics/.
"Micellar Water," Mintel, Oct. 11, 2018, 4 pages. http://www.gnpd.com.
International Search Report and Written Opinion from PCT Application No. PCT/US2019/058819, dated Jan. 24, 2020.

* cited by examiner

*Primary Examiner* — Vera Afremova
(74) *Attorney, Agent, or Firm* — Workman Nydegger

(57) ABSTRACT

Compositions intended for application onto human hair, skin, and/or nails can include an antimicrobial effective amount of a preservative system containing: (a) from about 2 to about 5% by weight of a *Lactobacillus* ferment; (b) from about 2 to about 5% by weight of a *Cocos nucifera* with or without *Lactobacillus* ferment; (c) from about 0.1 to about 0.5% by weight of at least one co-preservative ingredient chosen from salicylic acid and a salt of a weak acid; and (d) from about 1 to about 10% by weight of a petroleum-free propanediol, all weights based on the total weight of the composition, wherein the composition has a pH ranging from about 4.8 to about 5.5.

22 Claims, 9 Drawing Sheets

PRESERVATIVE SYSTEMS AND COMPOSITIONS AND METHODS INCORPORATING SAME

FIELD OF THE INVENTION

The present disclosure is directed to a natural preservative system comprised of naturally derived ingredients. More particularly, the disclosure is directed to an association of naturally derived ingredients that are not conventionally used as primary antimicrobial agents, which, in combination, surprisingly provide superior broad-spectrum preservation of compositions that are applied topically onto an end user's skin, hair, and/or nails.

BACKGROUND

Preservative formulations are a critical component of numerous consumer products, including cosmetic products like facial creams, face and body washes, or other products intended for application on the user's skin. Most of these products contain some amount of water, whether in the form of an oil-in-water and/or water-in-oil emulsion. The presence of an aqueous phase serves as a breeding ground for microbes, which over time cause the product to deteriorate and become unstable, a phenomenon typically referred to as microbial spoilage. Because microbes are abundantly present in the air and on users' skin, nearly any use of topical products is likely to introduce microbes, and if the product is not properly preserved, spoilage can occur within days of exposure to the microbes—thereby rendering the product unsafe and undesirable for use. Hence, the addition of some sort of preservative agent is imperative to prevent microbial spoilage and facilitate an acceptable shelf life for topical consumer products.

Preservative formulations have historically included synthetic or petroleum-derived additives that provide broad-spectrum protection against microbial growth at low concentrations and promote a long shelf-life. One major class of preservative traditionally used is commonly referred to as "parabens," which includes methyl, ethyl, propyl, and butyl esters of para-hydroxybenzoic acid. Higher esters are even more active than the butyl esters, but because of their decreased solubility, their use as a preservative has been limited. Benzoic acid may be used as either an acid or a salt, such as sodium benzoate. Regardless of form, the use of parabens has been considered hazardous to human health, causing the development of significant market pressures for the production of parab en-free products.

An early response to the consumer demand for paraben-free topical consumer products was the widespread use of phenoxyethanol as a preservative that was originally considered to be a safer "paraben alternative." Although the use of phenoxyethanol as a preservative is globally permitted in skin and cosmetic products in amounts of up to 1% by weight, conflicting research has brought its safety into question.

Problematically, phenoxyethanol tends to accumulate in live cells where it becomes toxic and deleterious to cellular function, and it is often included in cosmetics at levels in excess of regulations. Further, because phenoxyethanol is petroleum based, and ethoxylated, it is believed that exposure to phenoxyethanol is linked to various negative health reactions ranging from eczema to severe, life-threatening allergic reactions. Despite these concerns, the use of phenoxyethanol as a preservative remains quite prevalent. For example, phenoxyethanol is often utilized to supplement or boost other preservative ingredients, such as weak acids like salicylic, benzoic, levulinic, etc., thereby reducing the overall weight percent of the preservative formulation in the cosmetic product—often to 1% or less.

Other commonly used preservatives have received similar scrutiny and engender a reluctance on the part of consumers to use products that contain them. One such category of preservatives includes formaldehyde-releasing compounds like imidazolidinyl urea, diazolidinyl urea, 1,3-bis(hydroxymethyl)-5,5-dimethylimidazolidine-2,4-dione (also known as DMDM hydantoin), and quaternium-15. Many topical consumer products rely on either imidazolidinyl urea or diazolidinyl urea, alone or in combination with other preservatives such as parabens, to provide the requisite broad-spectrum protection against microbial growth. However, as with parabens, there is an increasing reluctance on the part of consumers to use products that contain formaldehyde-releasing preservatives. Exposure to formaldehyde is known to cause eye, nose, and throat irritation, and at sufficiently high levels can lead to skin rashes, shortness of breath, wheezing, changes in lung functions, and even cancer of at least the nose and throat. Children, the elderly, and people with preexisting breathing or lung conditions are especially vulnerable to formaldehyde's adverse health effects.

The use of harsh and frequently harmful chemicals like parabens and formaldehyde-releasing preservatives has been previously tolerated because of their effectiveness as effective, low-dose preservatives throughout the product's shelf life and, significantly, because of the prohibitive cost and difficulty of providing an effective "organic" or "natural" alternative. However, there is a strong consumer-led trend away from topical consumer products that include traditional hazardous or irritating preservatives and toward products that are deemed "organic" or "natural." In line with the philosophy of such products, consumers also expect them to be paraben free, phthalate free, sulfate free, silicone free, synthetic fragrance free, alcohol free, phenoxyethanol free, or otherwise non-toxic.

In response to the outstanding need in the industry for products that meet certain thresholds of "natural" and "organic" ingredients, coupled with the lack of official standards for what qualifies as "natural" and "organic," preservative formulation has become a cottage industry with consumers gravitating towards products containing natural extracts, botanicals, or other ingredients derived from natural sources, while avoiding those products having ingredients that are either known to cause or suspected of causing adverse health reactions. Unfortunately, this ad hoc approach and decentralization of acquired knowledge and experience of generating effective preservative formulations has led to a host of ineffective solutions that typically result in diminished shelf-life and usability of associated topical consumer products.

Various third-party certifications have been established in an attempt to bring consistency and reliability to the use of natural and organic preservatives in topical consumer products. For example, ECOCERT® is an organic certification organization based in Europe that conducts inspections in over 80 countries, making it one of the largest organic certification organizations in the world. ECOCERT® primarily certifies food and food products but also certifies cosmetics, detergents, perfumes, and textiles and is a leading certifier of fair-trade food, cosmetics, and textiles.

Another example is the Cosmetic Organic Standard (COSMOS), a Europe-wide private standard that was developed by five charter members: BDIH (Germany), Cosmebio (France), Ecocert Greenlife SAS (France), ICEA (Italy), and Soil Association (Great Britain). They were all combined under an AISBL (international non-profit organization based in Brussels), the purpose of which was to set out minimum common requirements, harmonize organic and natural cosmetic certification rules, and lobby institutions in the sector's interests. COSMOS makes use of the principles in the ECOCERT® standard: to promote the use of ingredients from organic farming, use production and manufacturing processes that are environmentally sound and safe for human health, and include and expand the concept of "green chemicals."

The National Organic Program (NOP), a federal regulatory framework in the United States governing organic food, is yet another certification. The core mission of the NOP is to protect the integrity of the United States Department of Agriculture (USDA) organic seal. The seal is used for products adhering to USDA standards that contain at least 95% organic ingredients.

Despite the certification systems pressuring the market to identify preservative systems as such and despite the upwelling demand and need for all-natural preservative systems, existing efforts have fallen short in identifying natural preservative formulations that omit harsh preservatives while also maintaining effective broad-spectrum protection. For instance, it is known that essential oils alone are insufficient as a broad-spectrum preservative and that there are few "green" alternatives to harsh synthetic/petroleum-based preservatives. Current efforts discourage the omission of phenoxyethanol from a preservative formulation because of the cost and volume associated with consequently increasing the remaining preservatives, e.g. an increase of about 500% by weight and cost.

Certain preservative formulations supplement natural ingredients, such as antimicrobial peptides secreted by *Lactobacillus* sp., with synthetic and/or harsh preservatives. For example, U.S. Pat. No. 9,700,507 utilizes phenoxyethanol in formulas having a pH less than 6 in combination with *Lactobacillus*-derived antimicrobial peptides. Of note, however, phenoxyethanol is necessarily provided in the preservative formulation in addition to the *Lactobacillus*-derived antimicrobial peptides to achieve the desired preservation characteristics.

The use of natural preservatives is also discussed in non-patent literature forums like "Bacteria Hack: Pre- and Probiotics in Skincare." Therein, *Lactobacillus* fermentation products, including antimicrobial peptides, are used to control the growth of microorganisms with a goal of maintaining a healthy balance of microbes on the user's skin while at the same time preserving compositions from microbial spoilage. It is discussed that antimicrobial peptides must be combined with the use of levulinic acid and anisic acid, among other ingredients, at a pH of 5.5 so as to maintain *Staphylococcus epidermidis* on a user's skin—thereby significantly narrowing the applicability and range of perseveration conditions.

Accordingly, existing efforts to create all-natural preservative formulations for cosmetics illustrate the difficulty of omitting harsh synthetic preservatives such as phenoxyethanol without compromising the effectiveness of the preservative formulation and are otherwise limited to the combination of antimicrobial peptides of *Lactobacillus*, levulinic acid, and anisic acid at a pH of 5.5 to preserve *S. epidermidis* colonization.

There remains a need for a broad-spectrum and natural preservative system for cosmetics and other topical consumer products that avoids the use of harsh preservatives.

Further, because of the need for safe and effective preservative formulations for consumer products and because of the challenges of existing natural preservative formulations to provide broad-spectrum protection in the absence of synthetic and undesirable ingredients, such as phenoxyethanol, there is a need for an improved preservative formulation utilizing only natural, green, and/or plant-based ingredients that provides effective broad-spectrum antimicrobial preservation. There is further a need for a preservative formulation that omits harsh preservatives such as parabens, formaldehyde-donors, and phenoxyethanol without compromising effective preservation.

An ideal preservative system kills and/or prevents the growth of a wide range of Gram-positive and Gram-negative bacteria, yeasts, and molds without fostering resistance to the preservative. It should be rapid acting and chemically and biologically stable throughout the manufacturing and packaging processes, as well as during storage prior to and after sale to a consumer—all while still providing in-container sanitization against repeated microbial challenge. Ideally, the system should be colorless, odorless and remain so throughout the expected shelf life of the product.

When considering commercialization, the total cost of a preservative system, its compatibility with other ingredients, and regulatory restrictions of its component parts can further complicate the selection and use of preservatives. Further, the particular choice and amount of preservative to be used within an ideal preservative system must be balanced to retain efficacy in killing and/or inhibiting the growth of microbes while at the same time not causing any deleterious health effects to the user, such as skin irritation and/or allergic sensitization. To this end, the preservative system should be natural and should comprise antimicrobial compounds in such combinations and proportions as to provide efficacious preservation while avoiding skin irritation.

Unfortunately, with all of the above-mentioned requirements and prohibitions, no single preservative agent or system has yet been identified that can accomplish these goals.

Hence, it is an object of the present disclosure to provide a natural preservative system having ingredients that are internationally acceptable (e.g., ECOCERT®-approved). Another object of the present disclosure is to provide a preservative system that can be successfully and efficaciously incorporated into an ECOCERT®-approved, natural, and organic product without negatively affecting the product's ECOCERT®, natural, and/or organic third-party certification. Yet another object is to provide an efficacious preservative system free of parabens, formaldehyde, phenoxyethanol and, in general, any petroleum-derived preservatives and ingredients. The preservative system is ideally natural and/or plant-based as opposed to synthetic.

SUMMARY

The present disclosure is directed to preservative systems and natural compositions including the same, as well as to methods for preventing and inhibiting microbial growth on compositions intended for application onto human skin, hair, and/or nails.

For example, a composition intended for application onto human skin, hair, and/or nails can include a preservative system having: (a) from about 1 to about 5%, preferably from about 2 to about 4%, by weight of a *Lactobacillus* ferment, (b) from about 1 to about 5%, preferably from about 2 to about 4%, by weight of a *Lactobacillus* and *Cocos nucifera* fruit extract, (c) up to about 0.5%, preferably from about 0.1 to about 0.45% and more preferably from about 0.2 to about 0.4%, by weight of at least one co-preservative ingredient chosen from salicylic acid or a salt of a weak acid, and (d) from about 1 to about 10%, preferably from about 2 to about 8% and more preferably from about 4 to about 6%, by weight of a petroleum-free propanediol, all weights based on a total weight of the composition, and the composition having a pH ranging from about 4.5 to about 5.5, preferably ranging from about 4.8 to about 5.3.

In one aspect, the at least one co-preservative ingredient is salicylic acid employed in an amount less than about 0.5%, preferably from about 0.2 to about 0.45% by weight, based on the total weight of the composition. Alternatively, the at least one co-preservative ingredient is a salt of a weak acid employed in an amount of from about 0.2 to about 0.4% by weight, based on the total weight of the composition. The salt of the weak acid can be, in at least one aspect, potassium sorbate. In embodiments, the at least one co-preservative ingredient can be a mixture of from about 0.2 to about 0.45% by weight of salicylic acid and from about 0.2 to about 0.4% by weight of a weak acid salt such as potassium sorbate, all weights based on the total weight of the composition.

In one aspect, the petroleum-free propanediol is employed in the preservative system in an amount from about 2 to about 8% by weight or from about 4 to about 6% by weight, based on the total weight of the composition.

In one aspect, the composition is natural, organic, ECO-CERT®-approved, and free of petroleum-derived ingredients.

In one aspect, the composition is free of any primary antimicrobial agents chosen from parabens, phenoxyethanol, formaldehyde donors, and combinations thereof.

In one aspect, the composition comprises a skin topic such as any one or more of a cream, lotion, serum, mist, spray, or wash.

In one aspect, the composition is intended for use on keratinous substances, including human hair and nails and can include any one or more of mascara, shampoo, nail polish, or conditioner.

According to another embodiment, a composition intended for application onto human skin includes an antimicrobial-effective amount of a preservative system having: (a) from about 2 to about 4% by weight of a *Lactobacillus* ferment, (b) from about 2 to about 4% by weight of a *Lactobacillus* and *Cocos nucifera* fruit extract, (c) from about 0.2 to about 0.45% by weight of salicylic acid, (d) from about 0.2 to about 0.4% by weight of potassium sorbate, and (e) from about 4 to about 6% by weight of a petroleum-free propanediol, all weights based on a total weight of the composition, and the composition having a pH ranging from about 4.5 to about 5.5, preferably ranging from about 4.8 to about 5.3.

In one aspect, the composition is natural, organic, ECO-CERT®-approved, and free of petroleum-derived ingredients and may additionally or alternatively be free of any primary antimicrobial agents chosen from parabens, phenoxyethanol, formaldehyde donors, and combinations thereof.

The present disclosure additionally extends to methods for preventing and inhibiting microbial growth on or in a composition intended for application onto human skin. An exemplary method includes adding to the composition an antimicrobial-effective amount of a preservative system containing: (a) from about 2 to about 4% by weight of a *Lactobacillus* ferment, (b) from about 2 to about 5% by weight of a *Lactobacillus* and *Cocos nucifera* fruit extract, (c) from about 0.1 to about 0.5% by weight of at least one co-preservative ingredient chosen from salicylic acid and a salt of a weak acid, and (d) from about 1 to about 10% by weight of a petroleum-free propanediol, all weights based on a total weight of the composition, wherein the composition has a pH ranging from about 4.5 to about 5.5, preferably from about 4.8 to about 5.3.

In one aspect, the at least one co-preservative ingredient within the preservative system of the applied composition is salicylic acid provided in an amount of from about 0.2 to about 0.45% by weight, based on the total weight of the composition. Additionally, or alternatively, the at least one co-preservative ingredient within the preservative system of the applied composition is potassium sorbate provided in an amount of from about 0.2 to about 0.4% by weight, based on the total weight of the composition. In embodiments, the at least one co-preservative ingredient within the preservative system of the applied composition can be a mixture of from about 0.2 to about 0.45% by weight of salicylic acid and from about 0.2 to about 0.4% by weight of a weak acid salt such as potassium sorbate, all weights based on the total weight of the composition.

In one aspect, the petroleum-free propanediol within the preservative system of the applied composition is provided in an amount from about 4 to about 6% by weight, based on the total weight of the composition. Additionally, or alternatively, both the composition and the preservative system are natural, organic, ECOCERT®-approved, free of petroleum-derived ingredients and free of any primary antimicrobial chosen from parabens, phenoxyethanol, formaldehyde donors, and mixtures thereof.

The present disclosure is additionally directed to preservative systems (e.g., for topical consumer products). An exemplary preservative system can include (a) from about 2 to about 8% by weight of a *Lactobacillus* ferment, (b) from about 2 to about 4% by weight of a *Lactobacillus* and *Cocos nucifera* fruit extract, (c) from about 0.2 to about 0.4% by weight of potassium sorbate, and (d) from about 4 to about 6% by weight of a petroleum-free propanediol, all weights based on a total weight of a composition into which the preservative system is applied, and the composition having a pH ranging from about 4.5 to less than about 5.5.

In one aspect, the preservative system includes from about 0.2 to about 0.45% by weight of salicylic acid. Additionally, or alternatively, the composition into which the preservative system is applied has a pH ranging from about 5 to about 5.5, preferably ranging from about 4.8 to about 5.3.

In additional or alternative aspects, the preservative system has (a) about 4% *Lactobacillus* ferment, (b) about 4% by weight of a *Lactobacillus* and *Cocos nucifera* fruit extract, (c) about 0.2 by weight of potassium sorbate, and (d) about 4% by weight of a petroleum-free propanediol, or has (a) about 4% *Lactobacillus* ferment, (b) about 4% by weight of a *Lactobacillus* and *Cocos nucifera* fruit extract, (c) about 0.4% by weight of potassium sorbate, and (d) about 4% by weight of a petroleum-free propanediol.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Figure 1:
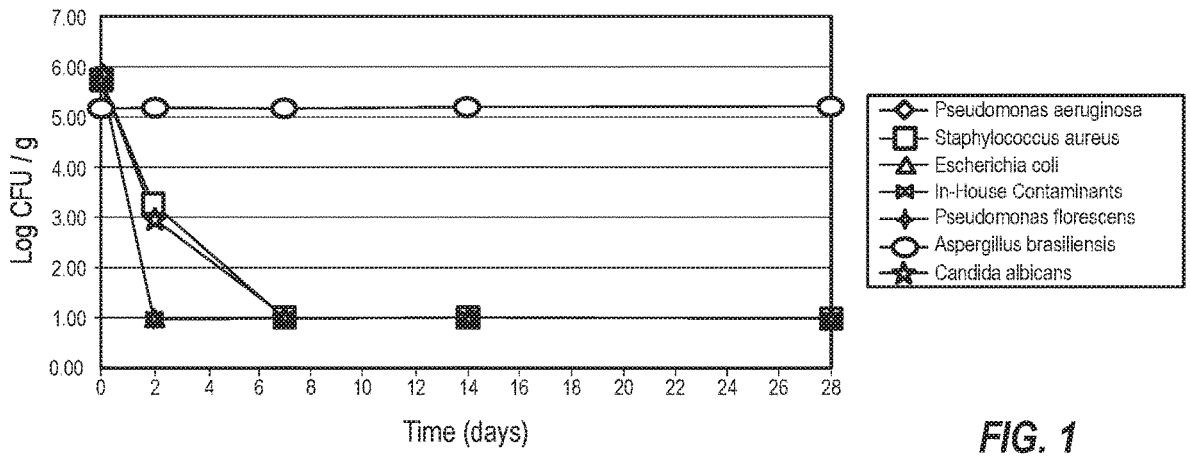
FIG. 1 illustrates the results of a microbial challenge assay using a traditional ECOCERT®-approved preservative system.

As described above, there is an outstanding need for natural preservative systems that include ingredients that are internationally acceptable and that can be successfully and efficaciously incorporated into ECOCERT®-approved, natural, and organic products without negatively affecting the products' ECOCERT®, natural, and/or organic third-party certification. An ideal natural preservative system satisfying the outstanding market need would be free of parabens, formaldehyde donors, phenoxyethanol and, in general, any petroleum-derived preservatives and ingredients.

However, it has proven difficult to identify a preservative system that meets these heightened standards. Preservative systems have traditionally relied on harsh chemicals, like parabens, to achieve the desired broad-spectrum protection, but when moving away from paraben-based systems, formulators relied on other toxic or irritating ingredients—principal among which are phenoxyethanol and the class of formaldehyde-releasing compounds. Phenoxyethanol has been scrutinized for its negative effects on human health, which range from eczema to severe, life-threatening allergic reactions. As with parabens and phenoxyethanol, there is also an increasing reluctance on the part of consumers to use products that contain formaldehyde-releasing compounds, formaldehyde being known for causing eye, nose, and throat irritation as well as rashes, adverse lung effects, and cancer.

In the absence of the canonical compounds that have been used for decades as the foundation for preservative systems, it has been particularly challenging to identify an alternative preservative system that consistently provides broad-spectrum protection while still meeting the stringent requirements of being all-natural, organic, and free of petroleum-derived preservatives and ingredients. As a result, a grass roots movement of do-it-yourself formulators have turned an activity that used to be performed by academic and commercial institutions into a cottage industry. Unfortunately, the formulations coming out of this cottage industry are unreliable and inconsistent, if not wholly ineffective.

Online tools have even been created to support the cottage industry of do-it-yourself formulators, such as "Making Skincare," a free, online skincare formulation course. This course discusses the need for preservatives and the concepts of broad-spectrum preservation, includes tutorials for conducting a microbial challenge assay to test the efficacy of various formulations, and provides a list of factors impacting the effectiveness of preservative systems generally. Of note, this course additionally includes a list of preservatives and their effectiveness and provides suggestions of when to use each to achieve broad-spectrum preservation.

Outside of the foregoing online course, there is little guidance provided by the longstanding commercial and academic institutions or the grass roots community of do-it-yourself formulators as to what ingredients can be used to create an acceptable natural and organic preservative system. Instead of avoiding all of the unfavorable preservatives, most formulators, including the online formulation course, have moved away from recommending the two biggest offenders—parabens and formaldehyde-releasing compounds—but have maintained phenoxyethanol as a foundational compound in their preservative systems as a booster that reduces the amount of other preservatives that are needed to achieve a desired level of efficacy.

It has been surprisingly discovered by the inventors that the combination of specific amounts of: a *Lactobacillus* ferment, a *Lactobacillus* and *Cocos nucifera* (coconut) fruit extract, salicylic acid (in some embodiments optional), potassium sorbate (in some embodiments optional), and a petroleum-free 1,3-propanediol, when incorporated into a composition intended for application onto human skin, hair, and/or nails (e.g., a topical consumer product) having a specific pH range, performs effectively as a preservative system to both prohibit and inhibit microbial growth on and in the associated composition without irritating the user's skin. Notably, the preservative systems disclosed herein exclude phenoxyethanol as well as parabens and formaldehyde-releasing compounds. Further, two of the main ingredients of the disclosed preservative systems—namely a *Lactobacillus* ferment and a *Lactobacillus* and *Cocos nucifera* fruit extract—have been indicated as "poor" preservatives against bacterial contaminants. However, when combined with the other components of the disclosed preservatives systems and calibrated to a defined pH range, a safe, effective, and reproducible all-natural and organic preservative system is obtained.

The disclosed preservative systems solve one or more of the problems in the art of all-natural and organic preservative systems. For example, the disclosed preservative systems include ingredients that are internationally acceptable and can be successfully and efficaciously incorporated into ECOCERT®-approved, natural, and organic products without negatively affecting the products' ECOCERT®, natural, and/or organic third-party certification.

The *Lactobacillus* ferment of the present disclosure is preferably employed in an amount of from about 1 to about 5% by weight, preferably from about 2 to about 4%, by weight of the total composition. An exemplary *Lactobacillus* ferment is commercially available from Active Micro Technologies under the tradename Leucidal® SF.

The *Lactobacillus* and *Cocos nucifera* fruit extract can include any *Cocos nucifera* fruit extract fermented with *Lactobacillus* and/or included with *Lactobacillus* ferment of the present disclosure and is preferably employed in an amount of from about 1 to about 5%, preferably from about 2 to about 4%, by weight of the total composition. An exemplary *Lactobacillus* and *Cocos nucifera* extract is commercially available from Active Micro Technologies under the tradename Amticide® Coconut and is typically associated with the International Nomenclature of Cosmetic Ingredients (INCI) name of a *Lactobacillus* and *Cocos nucifera* (coconut) fruit extract.

When present, salicylic acid is preferably employed in an amount of up to about 0.5% by weight, preferably from about 0.1 to about 0.45% and more preferably from about 0.2 to about 0.4%, by weight of the total composition. It should be noted that the use of salicylic acid in an amount at or greater than about 0.5% by weight, based on the total weight of the composition, renders the composition a drug requiring FDA approval in the prior to commercialization and sale in the United States. In some embodiments, salicylic acid may be omitted by adjusting the concentrations of *Lactobacillus* ferment, *Lactobacillus* and *Cocos nucifera* fruit extract, and/or other ingredients as described in greater detail herein.

When present, the salt of a weak acid is preferably employed in an amount of up to about 0.5% by weight, preferably from about 0.1 to about 0.45% and more preferably from about 0.2 to about 0.4%, by weight of the total composition. A preferred salt of a weak acid is potassium sorbate (i.e., the potassium salt of sorbic acid). Other weak acids that may be used in their salt form include, but are not limited to, acetic acid, propionic acid, and benzoic acid.

Petroleum-free 1,3-propanediol is typically employed in an amount of about 1 to about 10% by weight, preferably from about 2 to about 8% and more preferably from about 4 to about 6%, by weight of the total composition. An exemplary petroleum-free 1,3-propanediol is commercially available from Dupont Tate & Lyle Bio Products under the tradename Zemea® Propanediol and can be associated with the INCI name propanediol.

Embodiments of the present disclosure include preservative systems incorporated into topical consumer products that effectively provide broad-spectrum antimicrobial properties to the associated product. As used herein, the term "topical consumer product" is intended to include those compositions that are intended for application to the hair, skin, and/or nails. Topical consumer products include, for example, personal care products (e.g., deodorants, body washes, facial washes and cleansers, etc.), cosmetics (e.g., lip balms, chap sticks, lip glosses, primers, foundations, powders, sprays, concealers, etc.), skin care products (e.g., lotions, creams, sunscreens, scalp tonics, sprays, etc.), hair care products (e.g., shampoos, conditioners, hair masques, hair tonics, mascaras, sprays, styling products, etc.), anti-aging products, cosmeceuticals, nutraceuticals, and pharmaceuticals.

For purposes of the present disclosure, the use of the word "natural" is intended to encompass ECOCERT®-approved ingredients or formulations synonymous with the terms "green," "clean," "organic," "sustainable," "eco-friendly," or "environmentally-friendly" as known and used in the art. The term "natural," for example, may be used in the context of holistic or homeopathic formulations and is intended to include those topical consumer products and/or preservative systems that are plant-based, paraben-free, and/or non-toxic.

Further, when used in the context of the antimicrobial properties of a preservative or preservative system, the term "broad spectrum" is intended to describe those preservatives or preservative systems of the present disclosure that have the ability to inhibit the growth of or kill a wide range of microorganisms that decay or spoil topical consumer products. For example, a "broad spectrum" preservative system inhibits the growth of or kills a wide range of bacteria and fungi, preferably a wide range of Gram-positive and Gram-negative bacteria, yeasts, molds, and/or other fungi.

An exemplary broad-spectrum preservative system can include (a) from about 1 to about 5%, preferably from about 2 to about 4%, by weight of a *Lactobacillus* ferment; (b) from about 1 to about 5%, preferably from about 2 to about 4%, by weight of a *Lactobacillus* and *Cocos nucifera* fruit extract; (c) up to about 0.5%, preferably from about 0.1 to about 0.45% and more preferably from about 0.2 to about 0.4%, by weight of at least one co-preservative ingredient chosen from salicylic acid and/or a salt of a weak acid; and (d) from about 1 to about 10%, preferably from about 2 to about 8% and more preferably from about 4 to about 6%, by weight of a petroleum-free propanediol, all weights based on a total weight of a composition into which the preservative system is applied. The inventors have surprisingly discovered that the ability of the disclosed preservative systems to effectively inhibit microorganism growth is critically dependent on the pH of the composition in which it is used. For example, if the preservative system is employed in a composition having a pH of 6, it fails to provide the requisite broad-spectrum protection needed for acceptable storage stability/shelf-life. Accordingly, the pH of a composition containing the preservative system of the present disclosure must be in a range of from about 4.5 to less than about 5.5, preferably ranging from about 4.5 to about 5.5, more preferably ranging from about 4.8 to about 5.3.

Thus, according to one embodiment of the present disclosure, there is provided a composition intended for application onto human skin that contains a preservative system including: (a) from about 1 to about 5%, preferably from about 2 to about 4% by weight, of a *Lactobacillus* ferment; (b) from about 1 to about 5%, preferably from about 2 to about 4% by weight, of a *Lactobacillus* and *Cocos nucifera* fruit extract; (c) up to about 0.45% by weight of salicylic acid; and (d) from about 0.1 to about 0.5% by weight, preferably from about 0.2 to about 0.4% by weight, of at least one salt of a weak acid, preferably potassium sorbate; and (e) from about 1 to about 10%, preferably from about 2 to about 8% by weight, and most preferably from about 4 to about 6% by weight of a petroleum-free 1-3 propanediol, all weights based on the total weight of the composition, wherein the composition has a pH ranging from about 4.5 to about 5.5, preferably ranging from about 4.8 to about 5.3.

In another embodiment of the present disclosure, there is provided a composition intended for application onto human skin that contains a preservative system having: (a) from about 1 to about 5%, preferably from about 2 to about 4% by weight, of a *Lactobacillus* ferment; (b) from about 1 to about 5%, preferably from about 2 to about 4% by weight of a *Lactobacillus* and *Cocos nucifera* fruit extract; (c) from about 0.1 to about 0.45% by weight, preferably from about 0.2 to about 0.4% of salicylic acid; (d) up to about 0.5% by weight, preferably from about 0.2 to about 0.4% by weight, of at least one salt of a weak acid, preferably potassium sorbate; and (e) from about 1 to about 10%, preferably from about 2 to about 8% by weight, and most preferably from about 4 to about 6% by weight, of a petroleum-free 1-3 propanediol, all weights based on the total weight of the composition, wherein the composition has a pH ranging from about 4.5 to about 5.5, preferably ranging from about 4.8 to about 5.3.

According to yet another embodiment of the present disclosure, there is provided a composition intended for application onto human skin, the composition containing a preservative system that includes: (a) from about 1 to about 5%, preferably from about 2 to about 4% by weight, of a *Lactobacillus* ferment; (b) from about 1 to about 5%, preferably from about 2 to about 4% by weight, of a *Lactobacillus* and *Cocos nucifera* fruit extract; (c) from about 0.1 to about 0.45%, preferably from about 0.2 to about 0.4% by weight, of salicylic acid; (d) from about 0.1 to about 0.5% by weight, preferably from about 0.2 to about 0.4% by weight, of at least one salt of a weak acid, preferably potassium sorbate; and (e) from about 1 to about 10%, preferably from about 2 to about 8%, and most preferably from about 4 to about 6% by weight of a petroleum-free 1-3 propanediol, all weights based on the total weight of the composition, wherein the composition has a pH ranging from about 4.5 to about 5.5, preferably ranging from about 4.8 to about 5.3.

In yet another embodiment of the present disclosure, there is provided a composition intended for application onto human skin, the composition containing a preservative system comprised of: (a) from about 2 to about 4% by weight of a *Lactobacillus* ferment; (b) from about 2 to about 4% by weight of a *Lactobacillus* and *Cocos nucifera* fruit extract; (c) from about 0.2 to about 0.4% by weight of salicylic acid; (d) from about 0.2 to about 0.4% by weight of at least one salt of a weak acid, preferably potassium sorbate; and (e) from about 4 to about 6% by weight of a petroleum-free 1-3 propanediol, all weights based on the total weight of the composition, wherein the composition has a pH ranging from about 4.5 to about 5.5, preferably ranging from about 4.8 to about 5.3.

According to yet another embodiment of the present disclosure, there is provided a composition intended for application onto human skin, the composition containing a preservative system comprised of: (a) from about 2 to about 4% by weight of a *Lactobacillus* ferment; (b) from about 2 to about 4% by weight of a *Lactobacillus* and *Cocos nucifera* fruit extract; (c) from about 0.2 to about 0.45% by weight of salicylic acid; (d) from about 0.2 to about 0.4% by weight of at least one salt of a weak acid, preferably potassium sorbate; and (e) from about 4 to about 6% by weight of a petroleum-free 1-3 propanediol, all weights based on the total weight of the composition, wherein the composition has a pH ranging from about 4.5 to about 5.5, preferably ranging from about 4.75 to about 5.6.

The preservative system of the present disclosure may be incorporated into any natural, organic, green composition intended for application onto human skin. Moreover, both the preservative system itself, as well as the composition into which it is incorporated, satisfies the ECOCERT® standard. To be considered ECOCERT®-approved, a composition must: (1) use ingredients derived from renewable resources and be manufactured by environmentally friendly processes; and (2) contain a minimum threshold of natural ingredients from organic farming. Additional certifications for which the claimed disclosure qualifies include COSMOS and NOP.

The preservative system of the present disclosure is employed in any composition intended for application onto human skin. Examples thereof include, but are not limited to, topical consumer products, as that term is defined herein. The preservative system may also be employed in pharmaceutical products that are topically applied onto an end-user's body to treat a medical condition.

The term "comprising" as used herein is meant to include various optional, compatible components that can be used in the preservative systems and cosmetic compositions of the present disclosure. The term "consisting essentially of" as used herein means that the composition or component may include additional ingredients, but only if the additional ingredients do not materially alter the basic and novel characteristics of the compositions or methods.

As used herein, the words "preferred", "preferably" and variants thereof refer to embodiments of the disclosure that afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the disclosure.

Numerical ranges as used herein are intended to include every number and subset of numbers contained within that range, whether specifically disclosed or not. Further, these numerical ranges should be construed as providing support for a claim directed to any number or subset of numbers within that range.

All percentages, parts, proportions, and ratios as used herein are by weight of the total composition, unless otherwise specified. All such weights as they pertain to listed ingredients are based on the active level.

All references to singular characteristics or limitations of the present disclosure shall include the corresponding plural characteristic or limitation, and vice-versa, unless otherwise specified or clearly implied to the contrary by the context in which the reference is made.

All publications, articles, papers, patents, patent publications and other references cited herein are hereby incorporated in their entireties for all purposes to the extent consistent with the disclosure herein.

EXAMPLES

Beauty products are typically formulated to be stable over a period of 1-3 years from their date of manufacture and/or 1-2+ years from their date of first use. Cosmetic products, like virtually all products, have a limited shelf life and will naturally degrade over time. It is thus advised to perform stability testing on a product prior to releasing it to the public in order to ensure that it will remain safe to use during its shelf life.

Stability testing of cosmetics generally encompasses evaluating three categories of product stability, namely, microbiological stability, physical/chemical stability and packaging stability. It is generally not until a product achieves satisfactory results in all of these categories that it can be considered safe to use over the course of its intended shelf life.

Most skin care products, because they are intended to be used on a daily basis, are packaged in multi-dose containers, i.e., containers intended to be accessed multiple times. Each time a person accesses the contents of the container with their fingers, there is a risk that microorganisms present on their fingers may be introduced into the container and, once in, proliferate within the container rendering it contaminated. Once contaminated, continued use of the product may lead to serious infections, particularly in people with compromised skin that is dry, cracked, and inflamed due to, for example, acne breakouts.

In an effort to avoid or mitigate contamination, preservatives are added to the products to prevent or limit microbial contamination. The effectiveness of the preservative system can be enhanced or diminished depending on the specific preservatives used. Preservative efficacy testing (PET) is the process used to evaluate the effectiveness of a preservative system in a cosmetic product. The results of such a test are informative when evaluating the safety of a skin care product. The test involves introducing microorganisms into the product stored in its final retail packaging ("inoculating the product"), storing the inoculated product at a certain predetermined temperature, removing samples of the product at predetermined intervals of time, and counting the number of organisms present in the samples removed from the container. Inoculated products are thus periodically tested over a 28-day period. The effectiveness of the preservative system is considered acceptable if there is an initial drop in the number of microorganisms present in the product to a predetermined acceptable level or no appreciable increase in microorganisms within the product over the testing period.

The following examples as set forth herein are intended for illustrative purposes only and are not intended to limit the scope of the disclosure in any way.

Examples 1-10

The below-exemplified preservative systems were incorporated into a base formulation to determine their efficacy at inhibiting microbial growth on and/or in the base formulation when subjected to a microbial challenge assay. The base formulation included the ingredients listed in Table 1 in the noted concentration:

TABLE 1

| Ingredient | Concentration |
| --- | --- |
| Oil phase (waxes, oils, emulsifiers) | 20 |
| Water | 60 |
| Botanicals and Extracts | qs 100 |

Of note, the term "qs" is the Latin abbreviation for Quantum satis, meaning to add a sufficient amount. With respect to the base formulation provided in Table 1, the botanicals and extracts are added to 20 parts oil phase and 60 parts water in a sufficient amount for a final proportional concentration of 100 parts.

Each of the formulations exemplified below in Table 2 were added to the base formulation of Table 1 and subjected to microbial challenge to determine the formulations' ability to inhibit microbial growth both on and in the base formulation. The testing method protocol used was BP/EP 2012 appendix XVIC, incorporated herein by reference in its entirety.

TABLE 2

| | | Examples | | | | |
| --- | --- | --- | --- | --- | --- | --- |
| | Ingredient (INCI name) | 1 | 2 | 3 | 4 | 5 |
| Concentration (% weight) | Water/glycerin/sodium levulinate/anisate | | 4.0 | 4.0 | | |
| | Glyceryl caprylate | 0.4 | 0.4 | | | |
| | Peppermint/spearmint/clove/neem/rosemary oil | | 2.0 | 2.0 | | |
| | Orange/lemongrass/sesame seed oil | | | | 1.0 | |
| | Lactobacillus ferment | | | | 4.0 | 4.0 |
| | Lactobacillus Ferment & Cocos Nucifera | | | | 2.0 | 2.0 |

TABLE 2-continued

| Ingredient (INCI name) | Examples | | | | |
|---|---|---|---|---|---|
| | 1 | 2 | 3 | 4 | 5 |
| (Coconut) Fruit Extract | | | | | |
| Propanediol | | | 4.0 | 4.0 | 4.0 |
| pH | ~5 | ~5 | ~5 | ~5 | ~5 |
| Result | Fail | Fail | Fail | Fail | Fail |

Graphical representations of the results of microbial challenge assays performed for each formulation described in Examples 1-5 of Table 2 above are illustrated in FIG. 1-5, respectively. The pH values for Examples 1-5 were measured within a range of about 5.0 to about 5.5.

As seen in FIG. 1, the formulation of Example 1 failed to decrease the population of *Aspergillus brasiliensis* (*A. brasiliensis*) included in the microbial assay over the entire test period, while the populations of the other contaminants, including *Pseudomonas aeruginosa* (*P. aeruginosa*), *Staphylococcus aureus* (*S. aureus*), *Escherichia coli* (*E. coli*), In-House Contaminants, *Pseudomonas fluorescens* (*P. fluorescens*), and *Candida albicans* (*C. albicans*), were completely reduced. The populations of all other contaminants were decreased beginning on day 2, with *P. aeruginosa*, *E. coli*, In-House Contaminants, and *P. fluorescens* completely reduced by day 2 and *S. aureus* and *C. albicans* completely reduced by day 7. Because *A. brasiliensis* was not reduced, the formulation of Example 1 failed the microbial challenge assay.

Figure 2:
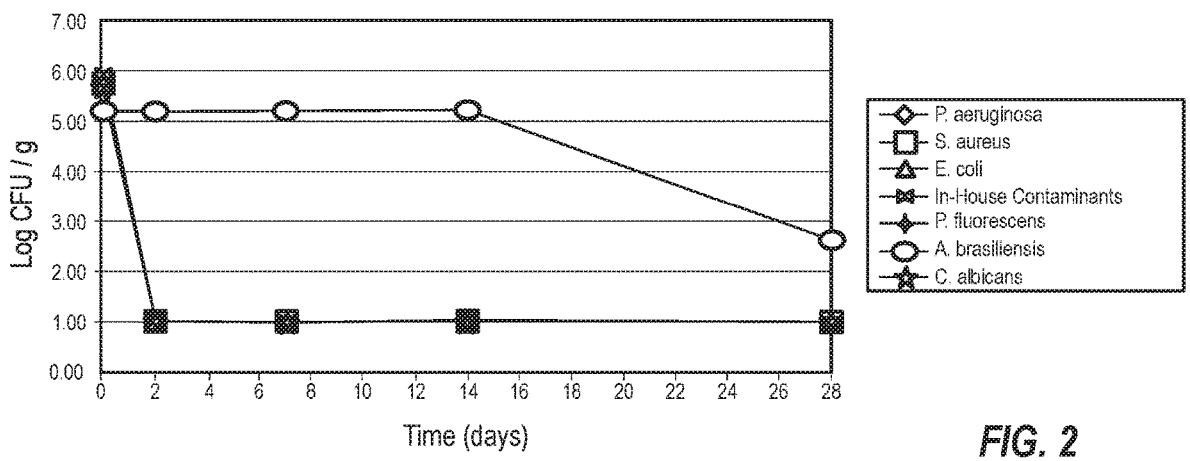
FIG. 2 illustrates the results of a microbial challenge assay using the preservative system of FIG. 1 augmented with essential oils.

As seen in FIG. 2, the formulation of Example 2 likewise failed to decrease the population of *A. brasiliensis* for 14 days, and by 28 days decreased the population without completely reducing the population. The other contaminants' populations were completely reduced by day 2. Because the population of *A. brasiliensis* was not completely reduced by day 28, the formulation of Example 2 failed the microbial challenge assay.

Figure 3:
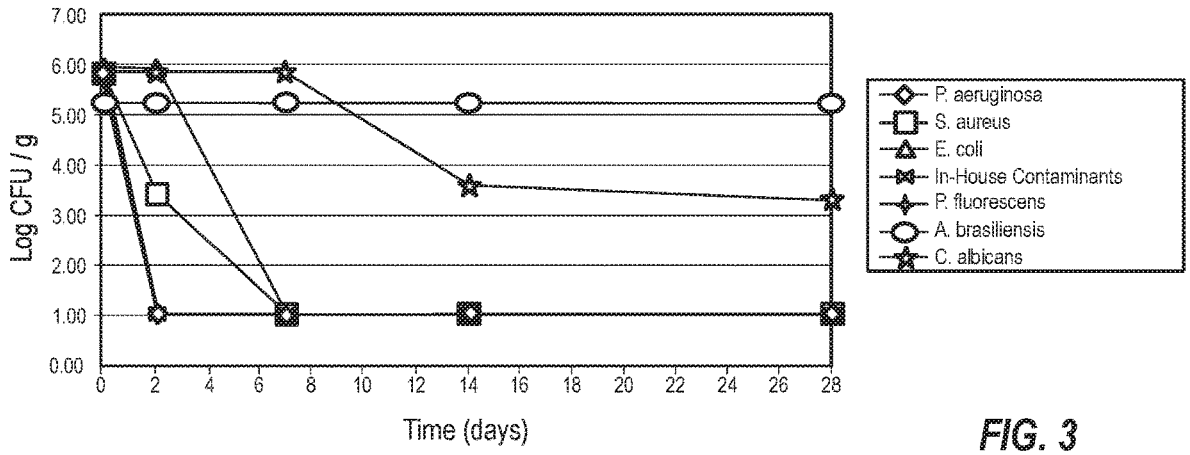
FIG. 3 illustrates the results of a microbial challenge assay using an exemplary all-natural preservative system.

As seen in FIG. 3, the formulation of Example 3 failed to completely reduce the populations of either *C. albicans* or *A. brasiliensis*. The populations of *P. aeruginosa*, In-House Contaminants, and *P. fluorescens* were completed reduced by day 2, and the populations of *E. coli* and *S. aureus* were completely reduced by day 7. The population of *C. albicans* was reduced starting on day 14, but by day 28, neither of the populations of *A. brasiliensis* and *C. albicans* were completely reduced. Because the populations of *A. brasiliensis* and *C. albicans* were not completely reduced, the formulation of Example 3 failed the microbial challenge assay.

Figure 4:
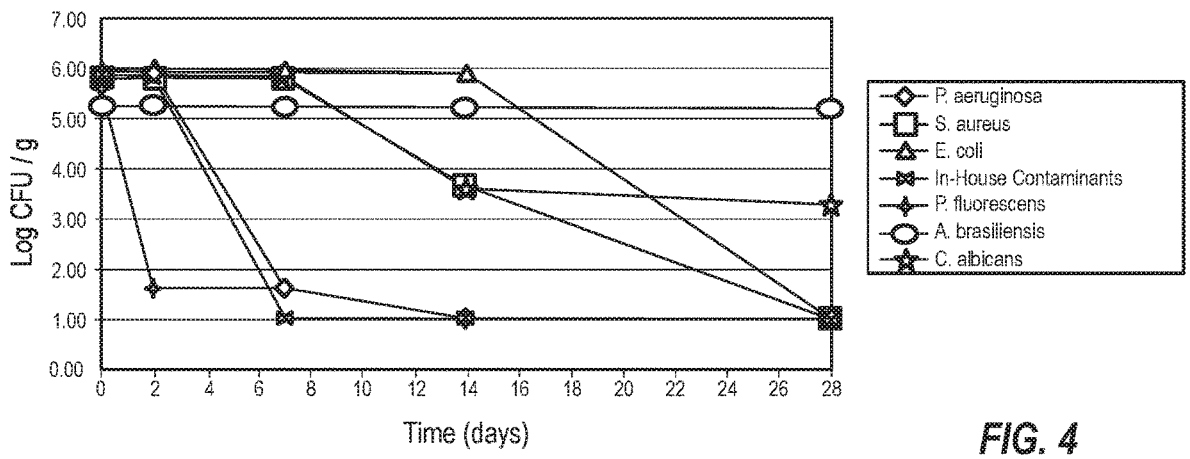
FIG. 4 illustrates the results of a microbial challenge assay using another exemplary all-natural preservative system.

As seen in FIG. 4, the formulation of Example 4 failed to completely reduce the populations of *C. albicans* or *A. brasiliensis*, and was slow to reduce the populations of *E. coli* and *S. aureus*, with complete reduction occurring only by day 28. The populations of *P. fluorescens* and *P. aeruginosa* were completely reduced by day 14 and the population of In-House Contaminants was completely reduced by day 7. Because the populations of *A. brasiliensis* and *C. albicans* were not completely reduced, the formulation of Example 4 failed the microbial challenge assay.

Figure 5:
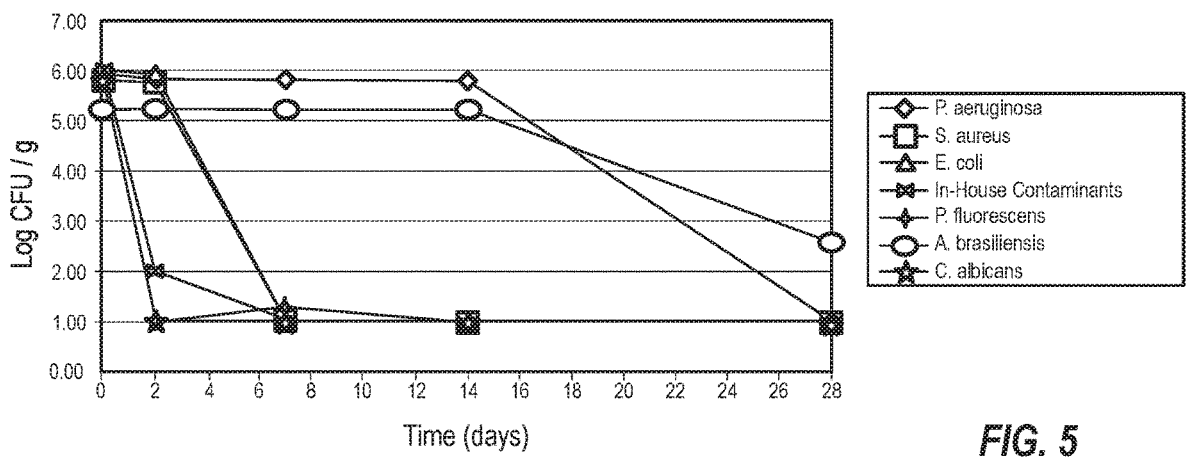
FIG. 5 illustrates the results of a microbial challenge assay using yet another exemplary all-natural preservative system.

As seen in FIG. 5, the formulation of Example 5 failed to completely reduce the population of *A. brasiliensis*. The populations of *C. albicans* and *P. fluorescens* were completely reduced by day 2 (with a brief growth of *P. fluorescens* at day 7 before being completely reduced by day 14). The populations of In-House Contaminants, *E. coli*, and *S. aureus* were completely reduced by day 7, and the population of *P. aeruginosa* was completely reduced by day 28. Because the population of *A. brasiliensis* was not completely reduced, the formulation of Example 5 failed the microbial challenge assay.

TABLE 3

| | Ingredient (INCI name) | Examples | | | | |
|---|---|---|---|---|---|---|
| | | 6 | 7 | 8 | 9 | 10 |
| Concentration (% weight) | *Lactobacillus* ferment | 4.0 | 4.0 | 4.0 | 4.0 | 4.0 |
| | *Lactobacillus* Ferment & *Cocos Nucifera* (Coconut) Fruit Extract | 2.0 | 2.0 | 2.0 | 4.0 | 4.0 |
| | Salicylic acid | 0.5 | 0.45 | 0.45 | | |
| | Propanediol | 4.0 | 4.0 | 4.0 | 4.0 | 4.0 |
| | Potassium sorbate | | 0.2 | 0.2 | 0.2 | 0.2 |
| | pH | 5.3 | 5.1 | 6.0 | 5.1 | 5.05 |
| | Result | Pass | Pass | Fail | Pass | Pass |

Graphical representations of the results of microbial challenge assays performed for each formulation described in Examples 6-10 of Table 3 above are illustrated in FIG. 6-10, respectively.

Figure 6:
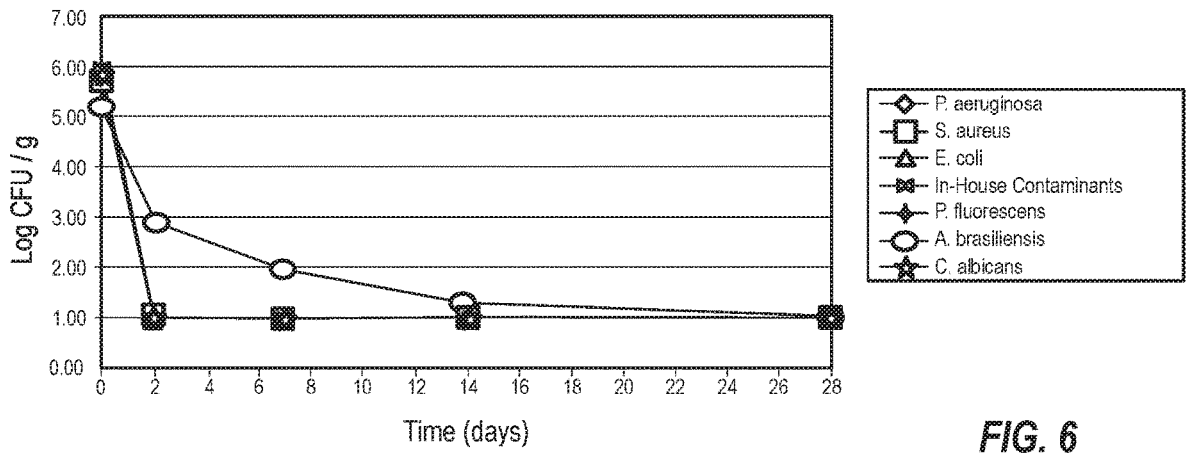
FIG. 6 illustrates the results of a microbial challenge assay using an exemplary preservative system according to one embodiment of the present disclosure.

As seen in FIG. 6, the formulation of Example 6 completely reduced the populations of all microbes, with *A. brasiliensis* completely reduced by day 28 and all other populations completely reduced by day 2. Because all populations were completely reduced, the formulation of Example 6 passed the microbial challenge assay.

Figure 7:
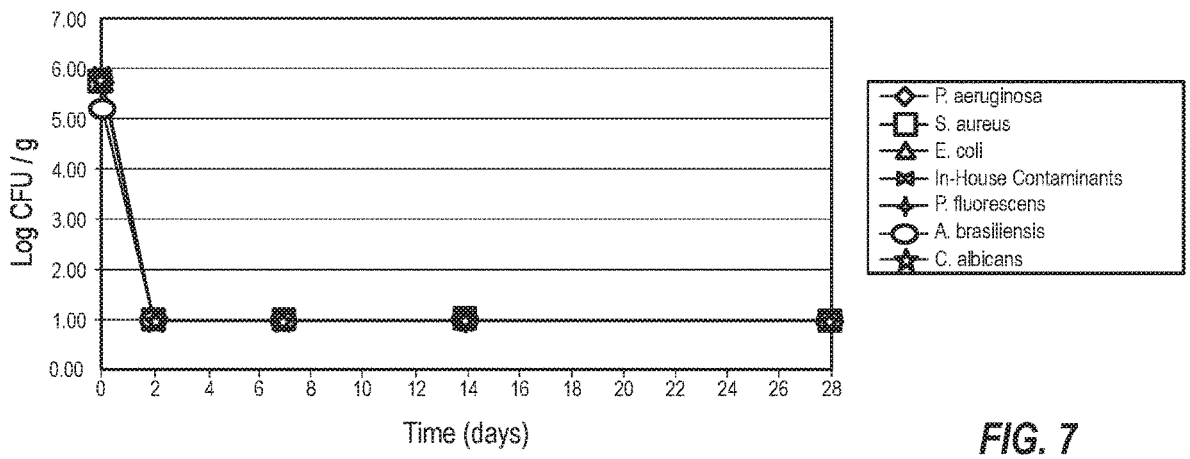
FIG. 7 illustrates the results of a microbial challenge assay using another exemplary preservative system according to one embodiment of the present disclosure.

As seen in FIG. 7, the formulation of Example 7 completely reduced the populations of all microbes, with all populations completely reduced by day 2. Because all populations were completely reduced, the formulation of Example 7 passed the microbial challenge assay.

Figure 8:
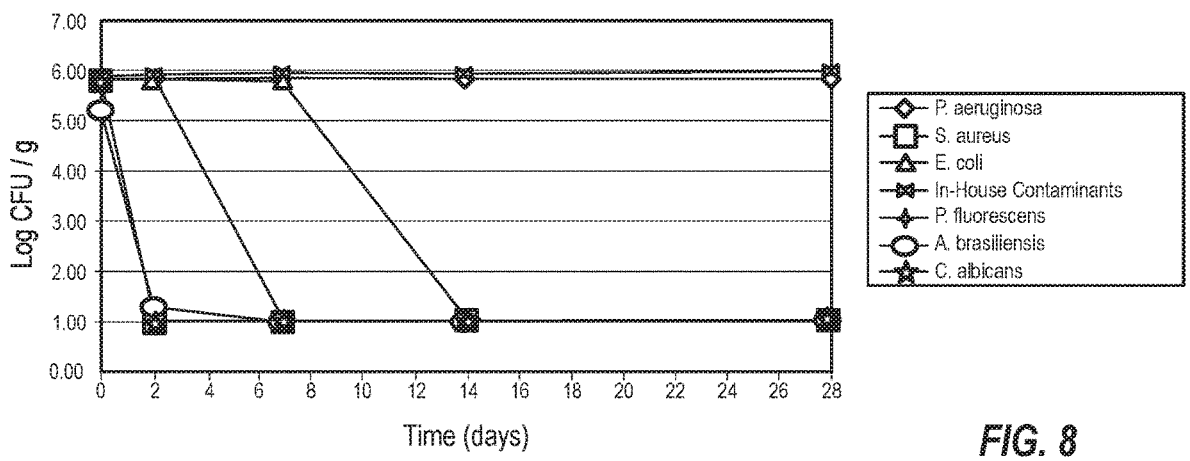
FIG. 8 illustrates the results of a microbial challenge assay using the preservative system of FIG. 7 having a pH of 6.

As seen in FIG. 8, the formulation of Example 8 did not completely reduce the populations of In-House Contaminants or *P. aeruginosa*. *A. brasiliensis* and *C. albicans* were completely reduced by day 7, while the population of *S. aureus* and *P. fluorescens* were completely reduced by day 2. The population *E. coli* was completely reduced by day 14. Because the populations of In-House Contaminants and *P. aeruginosa* were not completely reduced, the formulation of Example 8 failed the microbial challenge assay.

Figure 9:
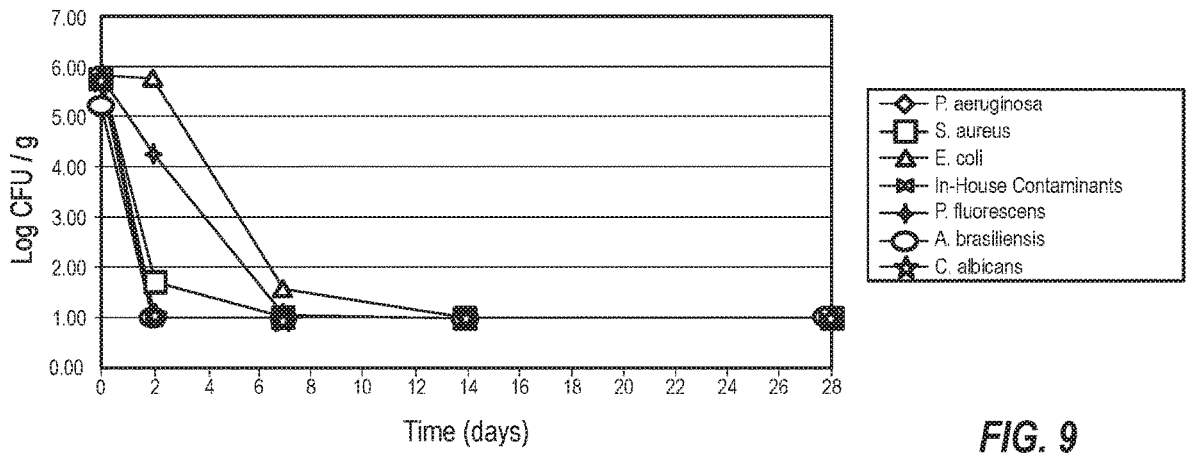
FIG. 9 illustrates the results of a microbial challenge assay using yet another exemplary preservative system according to one embodiment of the present disclosure.

As seen in FIG. 9, the formulation of Example 9 completely reduced the populations of all contaminants, with the populations of *A. brasiliensis*, *C. albicans*, In-House Contaminants, and *P. aeruginosa* completely reduced by day 2, the populations of *S. aureus* and *P. fluorescens* completely reduced by day 7, and the population of *E. coli* completely reduced by day 14. Because the populations of all contaminants were completely reduced, the formulation of Example 9 passed the microbial challenge assay.

Figure 10:
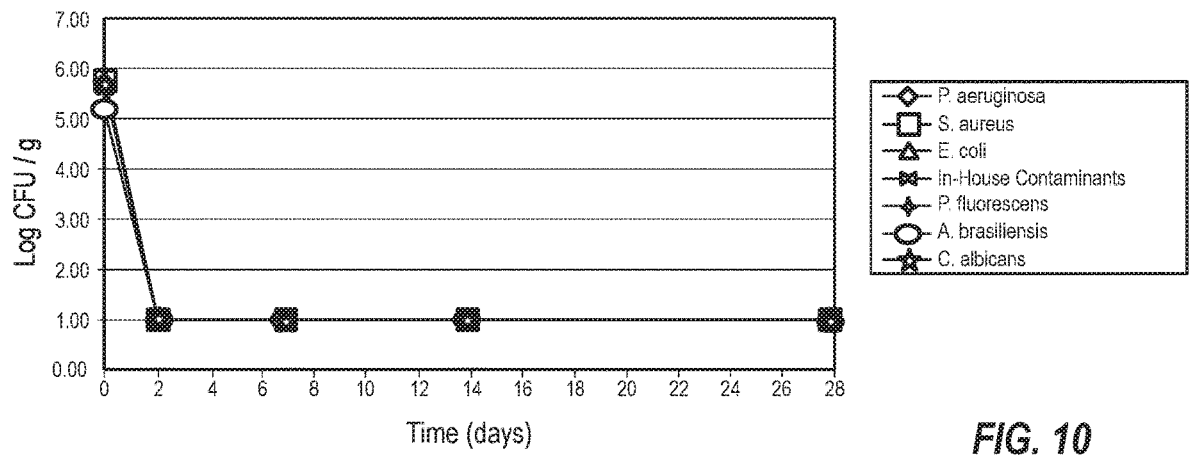
FIG. 10 illustrates the results of a microbial challenge assay using a modified version of the preservative system of FIG. 9.

As seen in FIG. 10, the formulation of Example 10 completely reduced the populations of all contaminants by day 2. Because the populations of all contaminants were completely reduced, the formulation of Example 10 passed the microbial challenge assay.

As can be seen from the examples in Tables 2 and 3 above (and corresponding FIG. 1-10), a preservative system comprising *Lactobacillus* ferment, *Cocos nucifera* fruit extract, salicylic acid, petroleum-free propanediol, and potassium sorbate at the prescribed pH in accordance with the present disclosure, when used in a composition intended for application onto human skin, hair, and/or nails, achieves broad-spectrum protection that effectively precludes and inhibits the growth of microorganisms on and in the composition. Since the preservative system itself qualifies for ECO- CERT®, natural and organic certifications, so long as the composition into which it is added (e.g., a topical consumer product) also possesses these certifications, the resultant composition will as well, thus satisfying consumers' needs for natural, organic and ECOCERT® products intended for application onto human skin, hair, and/or nails.

Examples 11-18

Additional preservative effectiveness tests were conducted using the microbial challenge assay described above to determine the in situ effectiveness of different preservative systems within an exemplary subset of topical consumer products. Two preservative systems were independently incorporated into an exemplary eye gel, skin moisturizer, face wash, and day cream, and the effectiveness of the preservatives was tested as above.

The first preservative system comprises the preservative system of Example 10, which for ease of illustration includes the components listed in Table 4 below.

TABLE 4

EXEMPLARY PRESERVATIVE SYSTEM #1

| Ingredients (INCI NAME) | Conc. (%) |
| --- | --- |
| *Lactobacillus* Ferment | 4.0 |
| *Lactobacillus* Ferment & *Cocos Nucifera* (Coconut) Fruit Extract | 4.0 |
| Potassium Sorbate | 0.4 |
| Propanediol | 4.0 |
| pH | 5.0-5.5 |

The second preservative system comprises a modified version of the preservative system described in Example 7, which for ease of illustration includes the components listed in Table 5 below, notably including salicylic acid at 0.45% by weight.

TABLE 5

EXEMPLARY PRESERVATIVE SYSTEM #2

| Ingredients (INCI NAME) | Conc. (%) |
| --- | --- |
| *Lactobacillus* Ferment | 4.0 |
| *Lactobacillus* Ferment & *Cocos Nucifera* (Coconut) Fruit Extract | 2.0 |
| Salicylic acid | 0.45 |
| Propanediol | 4.0 |
| Potassium Sorbate | 0.2 |
| pH | 5.0-5.5 |

It should be appreciated that the concentrations listed in Tables 4 and 5 are, with respect to the final concentration of each component, within a composition to be preserved by the respective preservative system.

Figure 11:
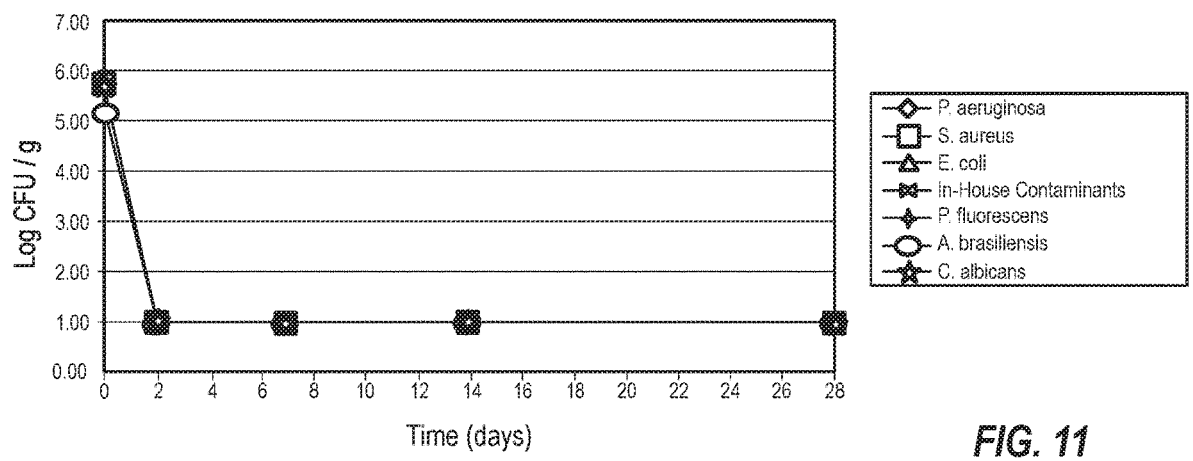
FIG. 11 illustrates the results of a microbial challenge assay using the preservative system of FIG. 7 incorporated into an exemplary eye gel composition in accordance with one embodiment of the present disclosure.
Figure 12:
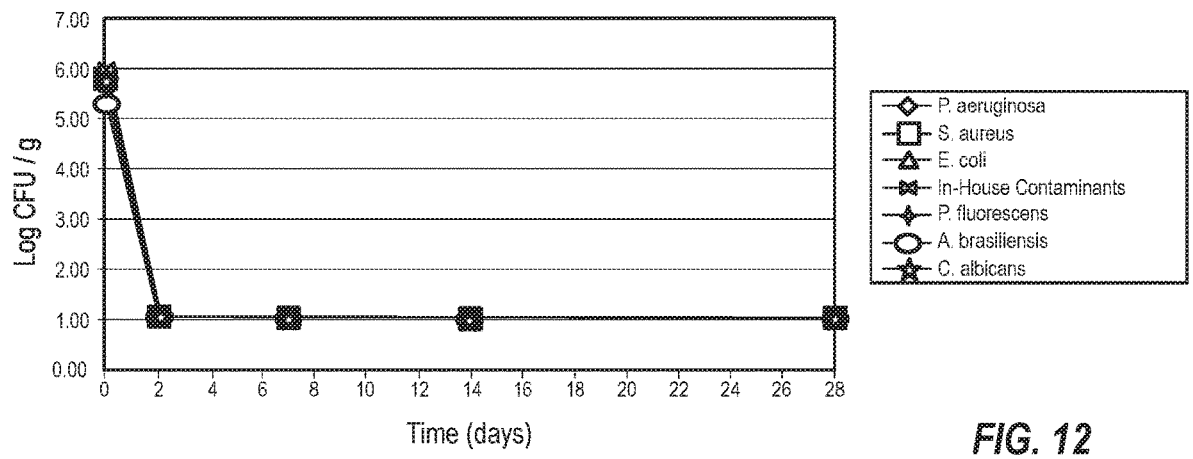
FIG. 12 illustrates the results of a microbial challenge assay using a modified version of the preservative system of FIG. 10 incorporated into an exemplary eye gel composition in accordance with one embodiment of the present disclosure.
Figure 13:
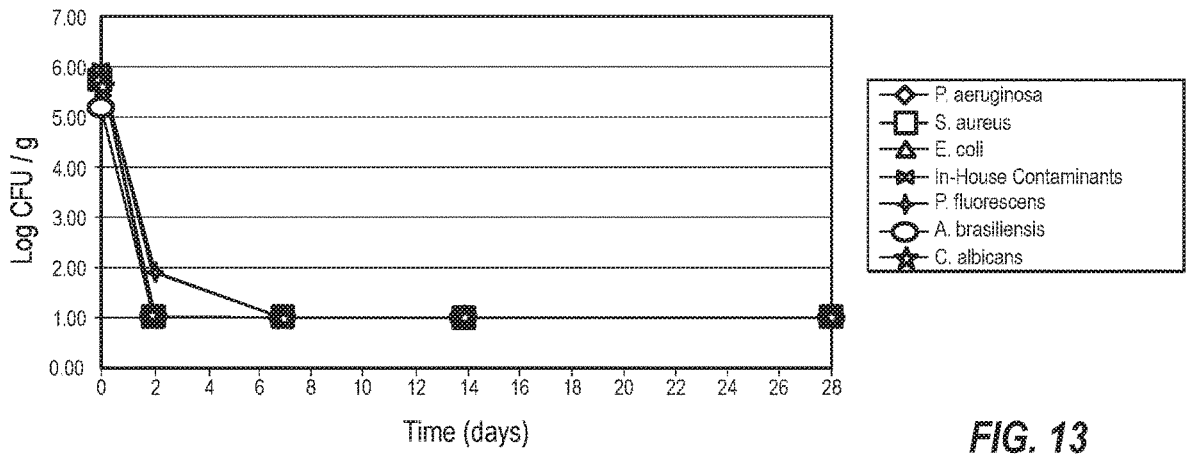
FIG. 13 illustrates the results of a microbial challenge assay using the preservative system of FIG. 7 incorporated into an exemplary topical consumer product in accordance with one embodiment of the present disclosure.
Figure 14:
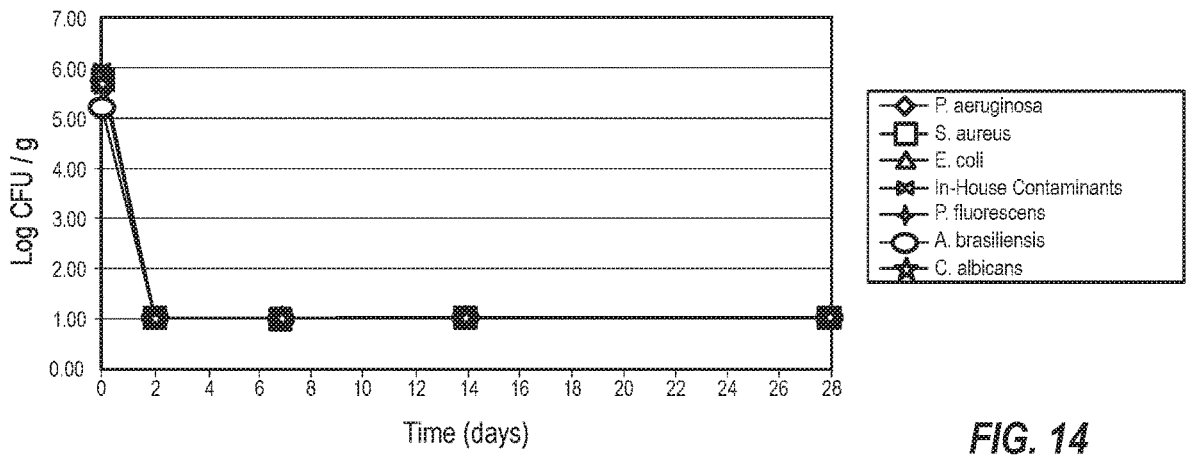
FIG. 14 illustrates the results of a microbial challenge assay using a modified version of the preservative system of FIG. 10 incorporated into an exemplary topical consumer product in accordance with one embodiment of the present disclosure.
Figure 15:
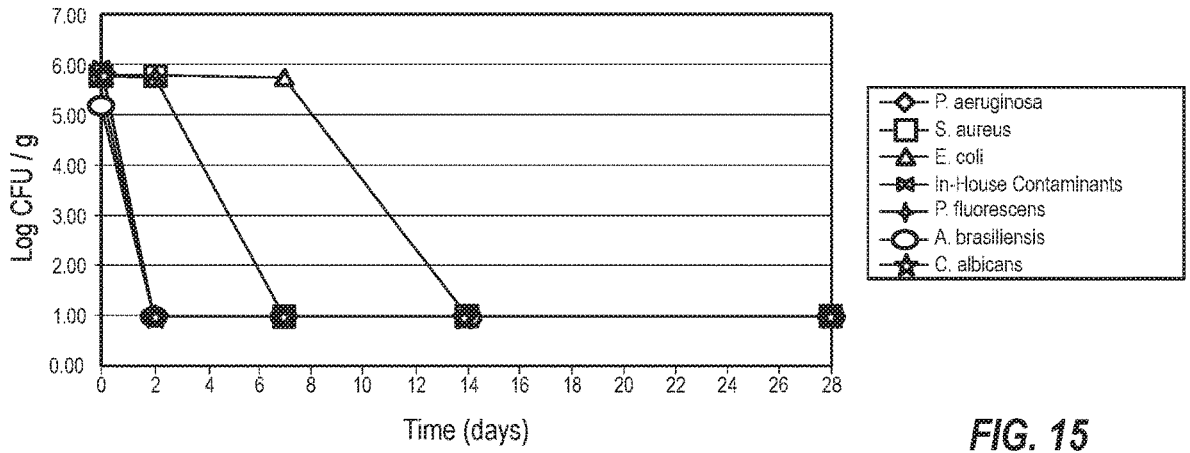
FIG. 15 illustrates the results of a microbial challenge assay using the preservative system of FIG. 7 incorporated into an exemplary facial wash composition in accordance with one embodiment of the present disclosure.
Figure 16:
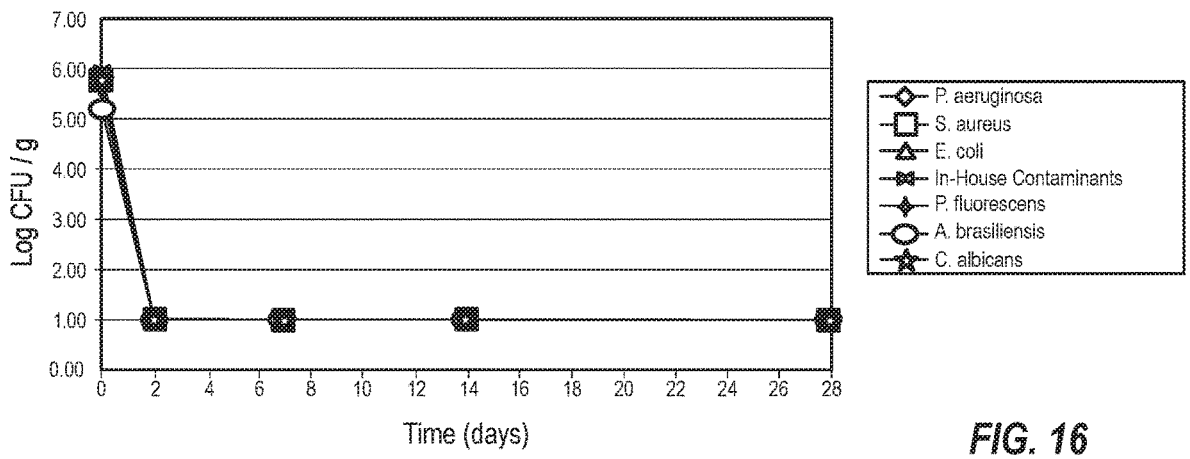
FIG. 16 illustrates the results of a microbial challenge assay using a modified version of the preservative system of FIG. 10 incorporated into an exemplary facial wash composition in accordance with one embodiment of the present disclosure.
Figure 17:
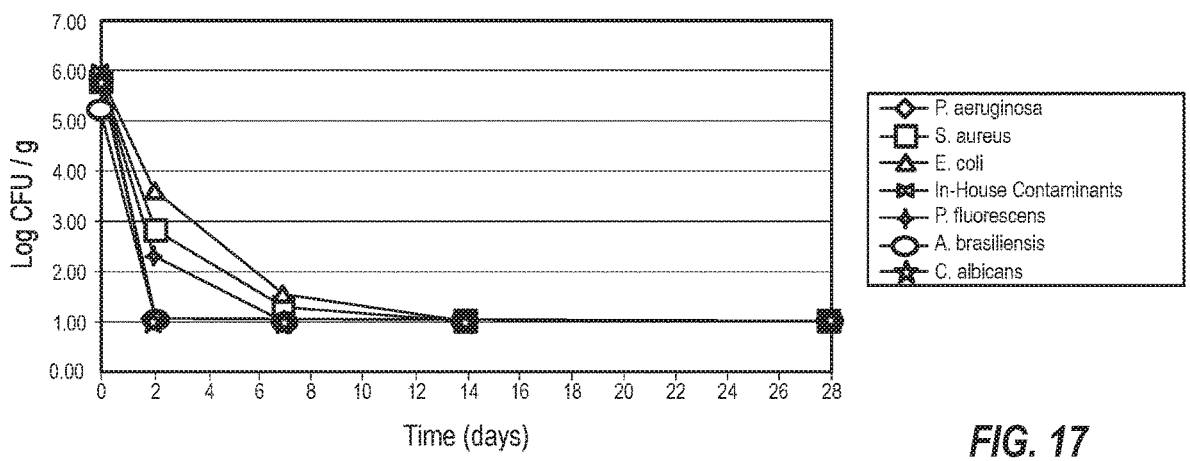
FIG. 17 illustrates the results of a microbial challenge assay using the preservative system of FIG. 7 incorporated into an exemplary day cream composition in accordance with one embodiment of the present disclosure.
Figure 18:
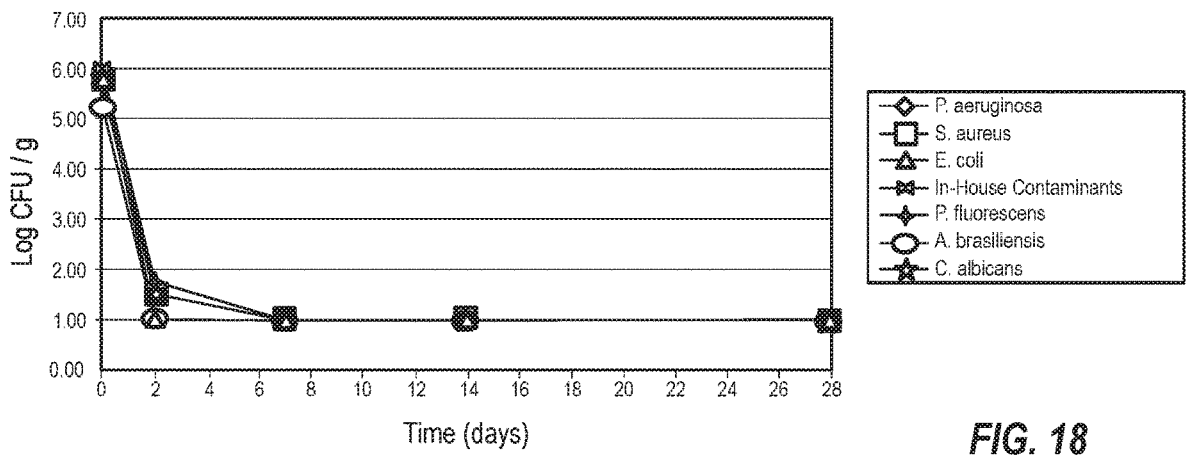
FIG. 18 illustrates the results of a microbial challenge assay using a modified version of the preservative system of FIG. 10 incorporated into an exemplary day cream composition in accordance with one embodiment of the present disclosure.

Graphical representations of the results of microbial challenge assays performed for each of the exemplary preservative systems listed in Tables 4 and 5 above are illustrated in FIG. 11-18, corresponding to Examples 11-18, respectively. In particular, the results for preservative systems 1 and 2 individually incorporated into an eye gel (i.e., Examples 11 and 12) are illustrated in FIGS. 11 and 12, respectively. The results for preservative systems 1 and 2 individually incorporated into a skin moisturizer (i.e., Examples 13 and 14) are illustrated in FIGS. 13 and 14, respectively. The results for preservative systems 1 and 2 individually incorporated into a face wash (i.e., Examples 15 and 16) are illustrated in FIGS. 15 and 16, respectively. The results for preservative systems 1 and 2 individually incorporated into a day cream (i.e., Examples 17 and 18) are illustrated in FIGS. 17 and 18, respectively.

As seen in FIG. 11, preservative system 1 when incorporated into an eye gel per Example 11 completely reduced the populations of all contaminants by day 2. Because the populations all contaminants were completely reduced, preservative system 1 passed the microbial challenge assay.

As seen in FIG. 12, preservative system 2 when incorporated into an eye gel per Example 12 completely reduced the populations of all contaminants by day 2. Because the populations all contaminants were completely reduced, preservative system 2 passed the microbial challenge assay.

As seen in FIG. 13, preservative system 1 when incorporated into a skin moisturizer per Example 13 completely reduced the populations of all contaminants by day 7, with only the population of *P. fluorescens* not completely reduced by day 2. Because the populations all contaminants were completely reduced, preservative system 1 passed the microbial challenge assay.

As seen in FIG. 14, preservative system 2 when incorporated into a skin moisturizer per Example 14 completely reduced the populations of all contaminants by day 2. Because the populations all contaminants were completely reduced, preservative system 2 passed the microbial challenge assay.

As seen in FIG. 15, preservative system 1 when incorporated into a face wash per Example 15 completely reduced the populations all contaminants by day 14. The populations of *A. brasiliensis, P. aeruginosa*, In-House Contaminants, and *P. fluorescens* were completely reduced by day 2, the populations of *S. aureus* and *C. albicans* were completely reduced by day 7, and the population of *E. coli* was completely reduced by day 14. Because the populations of all contaminants were completely reduced, preservative system 1 passed the microbial challenge assay.

As seen in FIG. 16, preservative system 2 when incorporated into a face wash per Example 16 completely reduced the populations of all contaminants by day 2. Because the populations all contaminants were completely reduced, preservative system 2 passed the microbial challenge assay.

As seen in FIG. 17, preservative system 1 when incorporated into a day cream per Example 17 completely reduced the populations of all contaminants. The populations of *A. brasiliensis*, In-House Contaminants, *P. fluorescens*, and *P. aeruginosa* were completely reduced by day 2, the population of *C. albicans* were completely reduced by day 7, and the populations of *S. aureus* and *E. coli* were completely reduced by day 14. Because the populations of all contaminants were completely reduced, preservative system 1 passed the microbial challenge assay.

As seen in FIG. 18, preservative system 2 when incorporated into a day cream per Example 18 completely reduced the populations of all contaminants. The populations of *E. coli, A. brasiliensis*, and *C. albicans* were completely reduced by day 2, and the populations of *S. aureus*, In-House Contaminants, *P. fluorescens*, and *P. aeruginosa* were completely reduced by day 7. Because the populations all contaminants were completely reduced, preservative system 2 passed the microbial challenge assay.

As shown in FIG. 11-18, all-natural, organic preservative systems of the present disclosure are free of parabens, formaldehyde-releasing compounds, and phenoxyethanol and are functional to reduce the microbial burden and prevent growth of microbes over time within topical consumer products.

Examples 19-25

Additional preservative effectiveness tests were conducted using the microbial challenge assay described above to determine the in situ effectiveness of a preservative system according to embodiments of the disclosure within an exemplary consumer product.

The preservative systems of Examples 19-25 shown below comprise a modified version of the preservative system described in Example 7, which for ease of illustration includes the components listed in Table 6 below, notably including salicylic acid at 0.45% by weight.

TABLE 6

| | Ingredient (INCI name) | Examples | | | | | | |
|---|---|---|---|---|---|---|---|---|
| | | 19 | 20 | 21 | 22 | 23 | 24 | 25 |
| Concentration (% weight) | Lactobacillus ferment | 4.0 | 4.0 | 4.0 | 4.0 | 4.0 | 4.0 | 4.0 |
| | Lactobacillus Ferment & Cocos Nucifera (Coconut) Fruit Extract | 4.0 | 4.0 | 4.0 | 4.0 | 4.0 | 4.0 | 4.0 |
| | Salicylic Acid | 0.45 | 0.45 | 0.45 | 0.45 | 0.45 | 0.45 | 0.45 |
| | Potassium Sorbate | 0.4 | 0.4 | 0.4 | 0.4 | 0.4 | 0.4 | 0.4 |
| | Propanediol | 4.0 | 4.0 | 4.0 | 4.0 | 4.0 | 4.0 | 4.0 |
| | pH | 4.76 | 4.48 | 4.99 | 5.24 | 5.55 | 5.73 | 6.00 |
| | Result | Pass | Pass | Pass | Pass | Pass | Fail | Fail |

As above, it should be noted that the preservative compositions of Table 6 are, with respect to the final concentration of each component, within a composition to be preserved by the respective preservative system.

Graphical representations of the results of microbial challenge assays performed for the exemplary preservative systems listed in Table 6 above are illustrated in FIG. 19-25, corresponding to Examples 19-25, respectively. In particular, the results for the preservative systems listed in Table 6 above were individually incorporated into a day cream moisturizer product.

Figure 19:
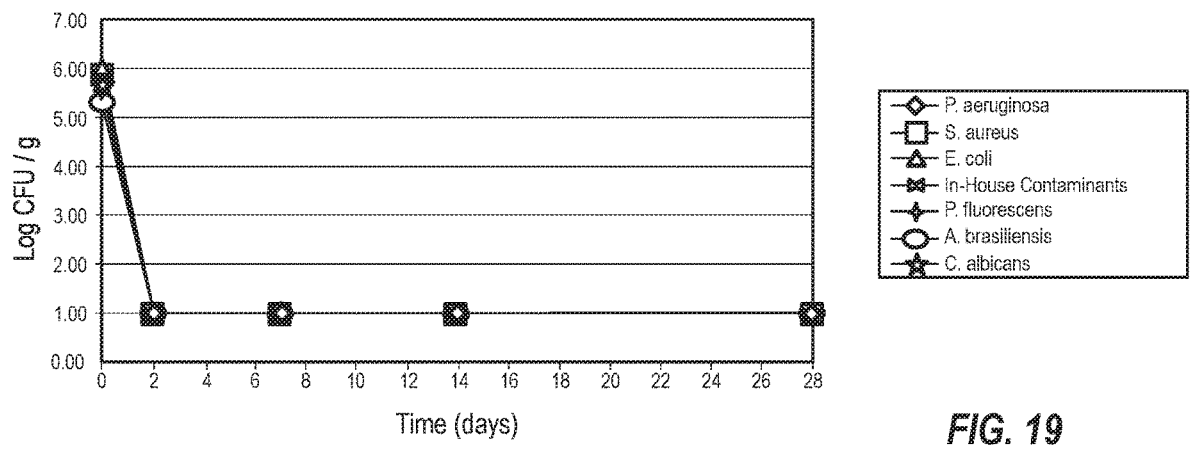
FIG. 19 illustrates the results of a microbial challenge assay using a modified version of the preservative system of FIG. 10 incorporated into an exemplary day cream composition in accordance with one embodiment of the disclosure.

As seen from FIG. 19, the preservative system of Example 19 completely reduced the populations of all contaminants by day 2. Because the populations of all contaminants were reduced, Example 19 passed the microbial challenge assay.

Figure 20:
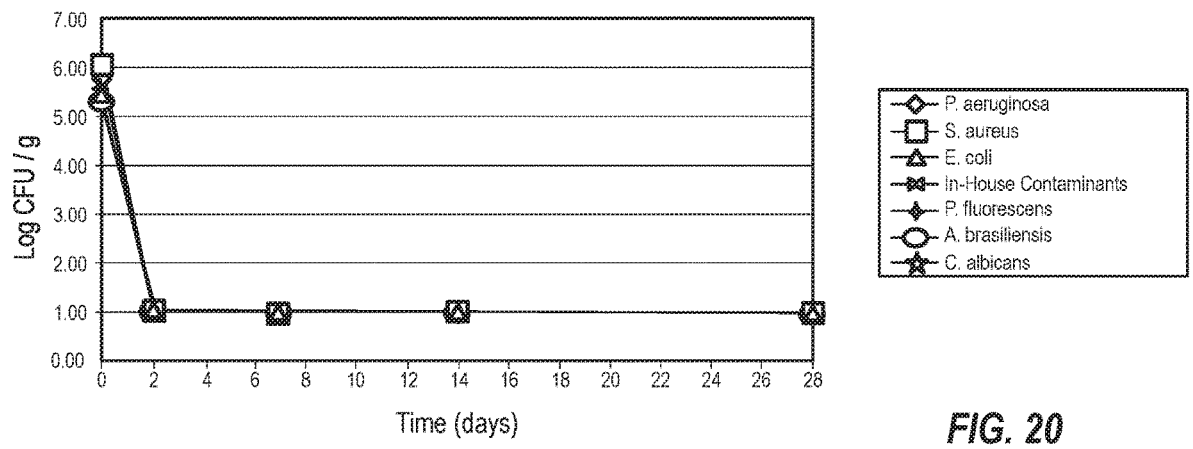
FIG. 20 illustrates the results of a microbial challenge assay using a modified version of the preservative system of FIG. 10 incorporated into an exemplary day cream composition in accordance with one embodiment of the disclosure.

As seen from FIG. 20, the preservative system of Example 20 completely reduced the populations of all contaminants by day 2. Because the populations of all contaminants were reduced, Example 20 passed the microbial challenge assay.

Figure 21:
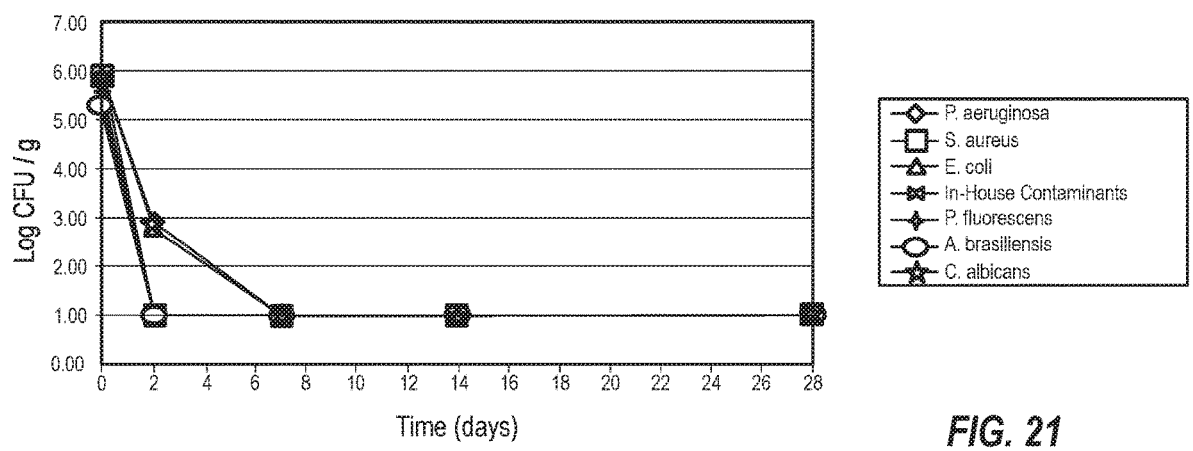
FIG. 21 illustrates the results of a microbial challenge assay using a modified version of the preservative system of FIG. 10 incorporated into an exemplary day cream composition in accordance with one embodiment of the disclosure.

As seen from FIG. 21, the preservative system of Example 21 completely reduced the populations of all contaminants, with the populations of *A. brasiliensis*, In-House Contaminants, *P. fluorescens*, and *P. aeruginosa* completely reduced by day 2, and the populations of *E. coli*, *S. aureus*, and *C. albicans* completely reduced by day 7. Because the populations of all contaminants were reduced, Example 21 passed the microbial challenge assay.

Figure 22:
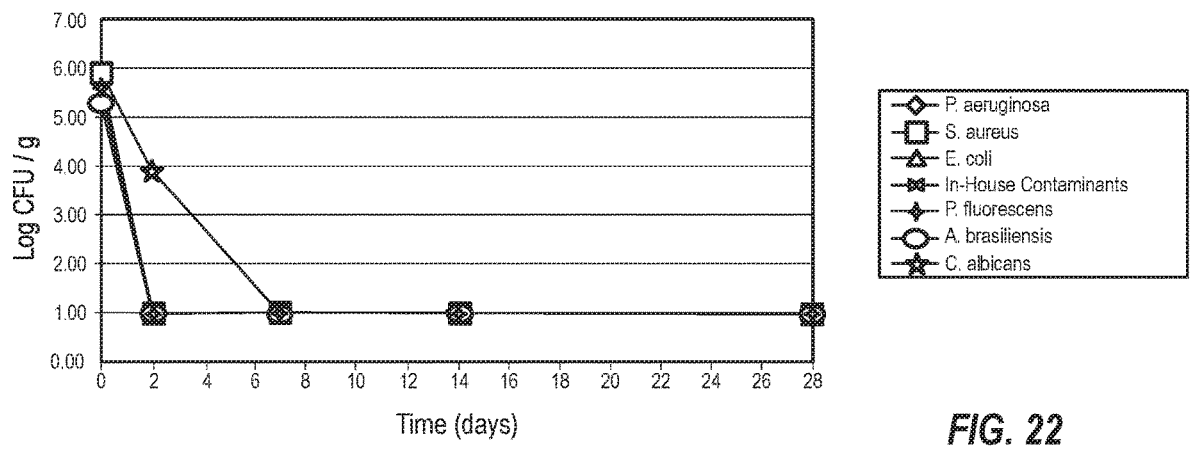
FIG. 22 illustrates the results of a microbial challenge assay using a modified version of the preservative system of FIG. 10 incorporated into an exemplary day cream composition in accordance with one embodiment of the disclosure.

As seen from FIG. 22, the preservative system of Example 22 completely reduced the populations of all contaminants, with the populations of *A. brasiliensis*, *P. fluorescens*, In-House Contaminants, *E. coli*, *S. aureus*, and *P. aeruginosa* completely reduced by day 2 and the population of *C. albicans* completely reduced by day 7. Because the populations of all contaminants were reduced, Example 22 passed the microbial challenge assay.

Figure 23:
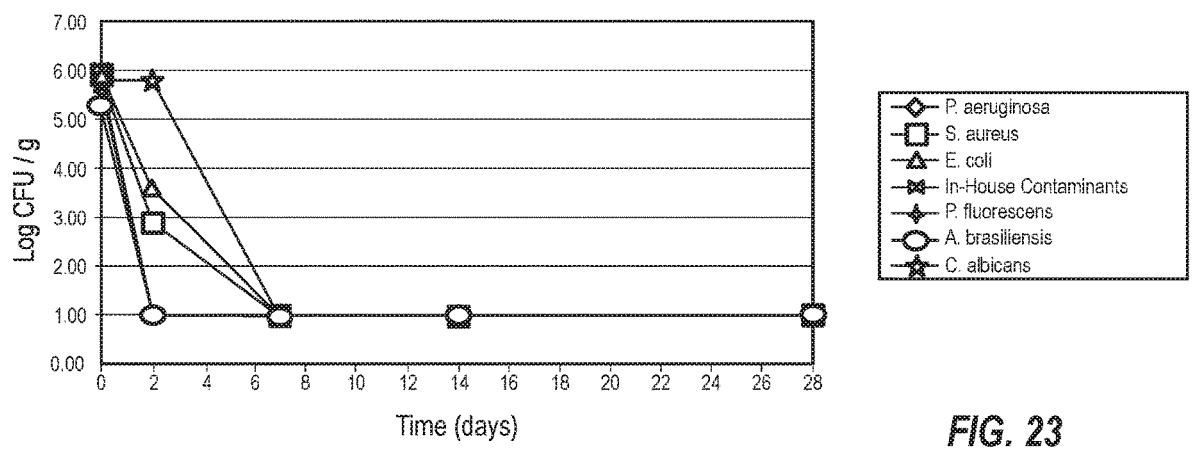
FIG. 23 illustrates the results of a microbial challenge assay using a modified version of the preservative system of FIG. 10 incorporated into an exemplary day cream composition in accordance with one embodiment of the disclosure.

As seen from FIG. 23, the preservative system of Example 23 completely reduced the populations of all contaminants, with the populations of *A. brasiliensis*, *P. fluorescens*, In-House Contaminants and *P. aeruginosa* completely reduced by day 2, and the populations of *S. aureus*, *E. coli*, and *C. albicans* completely reduced by day 7. Because the populations of all contaminants were reduced, Example 23 passed the microbial challenge assay.

Figure 24:
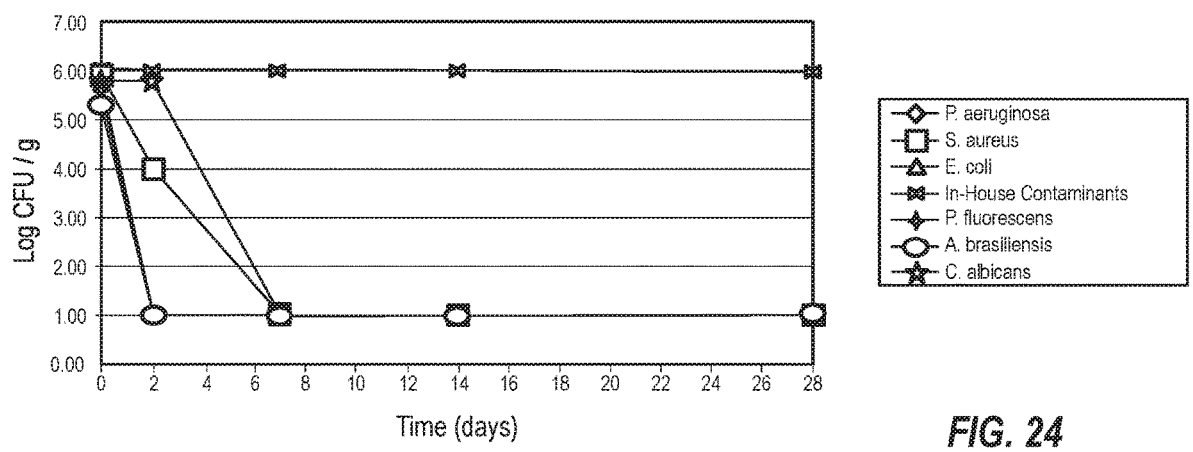
FIG. 24 illustrates the results of a microbial challenge assay using a modified version of the preservative system of FIG. 10 incorporated into an exemplary day cream composition in accordance with one embodiment of the disclosure.

As seen from FIG. 24, the preservative system of Example 24 did not completely reduce the populations of all contaminants, with the populations of *A. brasiliensis*, *P. fluorescens*, and *P. aeruginosa* completely reduced by day 2, and the populations of *S. aureus*, *E. coli*, and *C. albicans* completely reduced by day 7, while In-House Contaminants were not reduced. Because In-House Contaminants were not reduced, Example 24 failed the microbial challenge assay.

Figure 25:
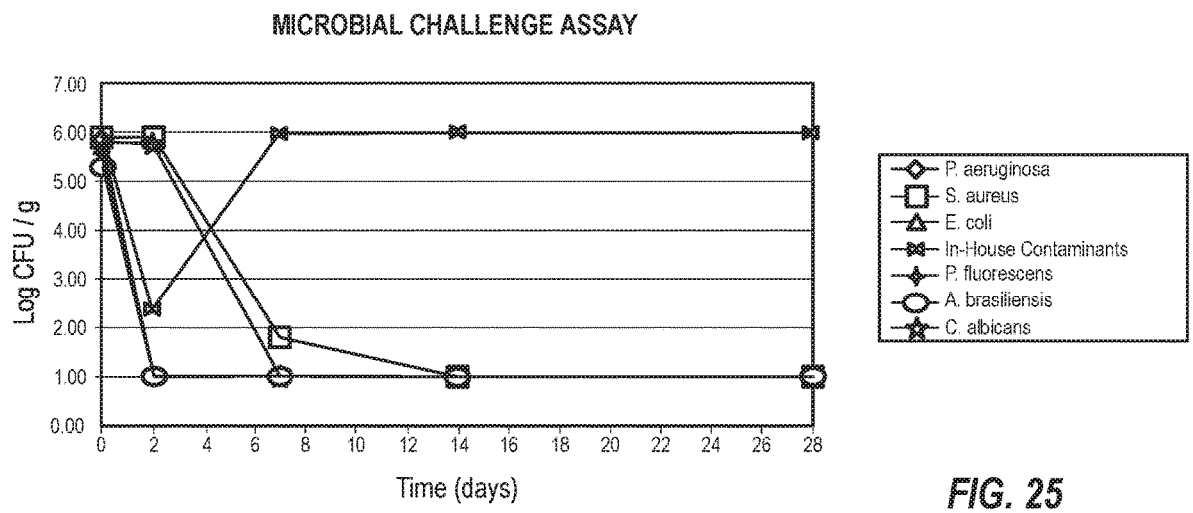
FIG. 25 illustrates the results of a microbial challenge assay using a modified version of the preservative system of FIG. 10 incorporated into an exemplary day cream composition in accordance with one embodiment of the disclosure.

As seen from FIG. 25, the preservative system of Example 25 did not completely reduce the populations of all contaminants, with the populations of *A. brasiliensis*, *P. fluorescens*, and *P. aeruginosa* completely reduced by day 2, the population of *E. coli* and *C. albicans* completely reduced by day 7, and the population of *S. aureus* completely reduced by day 14, while the population of In-House Contaminants were initially reduced by day 2 but were not completely reduced by day 28. Because In-House Contaminants were not reduced, Example 25 failed the microbial challenge assay.

As seen from Examples 19-25, a preservative system comprising *Lactobacillus* ferment, *Lactobacillus* Ferment & *Cocos Nucifera* (Coconut) Fruit Extract, Salicylic Acid, Potassium Sorbate, and Propanediol within a suitable pH range according to embodiments of the present disclosure can provide effective broad-spectrum protection in a cosmetic composition against microbial spoilage while using only natural ingredients and while also excluding phenoxyethanol, parabens, and formaldehyde donors which are universally applied in existing cosmetic preparations. In particular, it has been found that the preservative system according to the disclosure at a pH range of between 4.48 and 5.55 is effective at providing broad-spectrum protection, and that a pH above 5.73 is not effective at broad-spectrum or comprehensive protection.

Example 26

Additional preservative effectiveness tests were conducted using the microbial challenge assay described above to determine the in situ effectiveness of a preservative system having 0.2% salicylic acid according to embodiments of the disclosure within an exemplary consumer product.

The preservative systems of Example 26 comprise a modified version of the preservative system described in Examples 19-25, which for ease of illustration includes the components listed in Table 6 above, with the notable exception that salicylic acid is included at 0.2% by weight.

As above, it should be noted that the preservative compositions of Example 26 is, with respect to the final concentration of each component, within a composition to be preserved by the associated preservative system.

Figure 26:
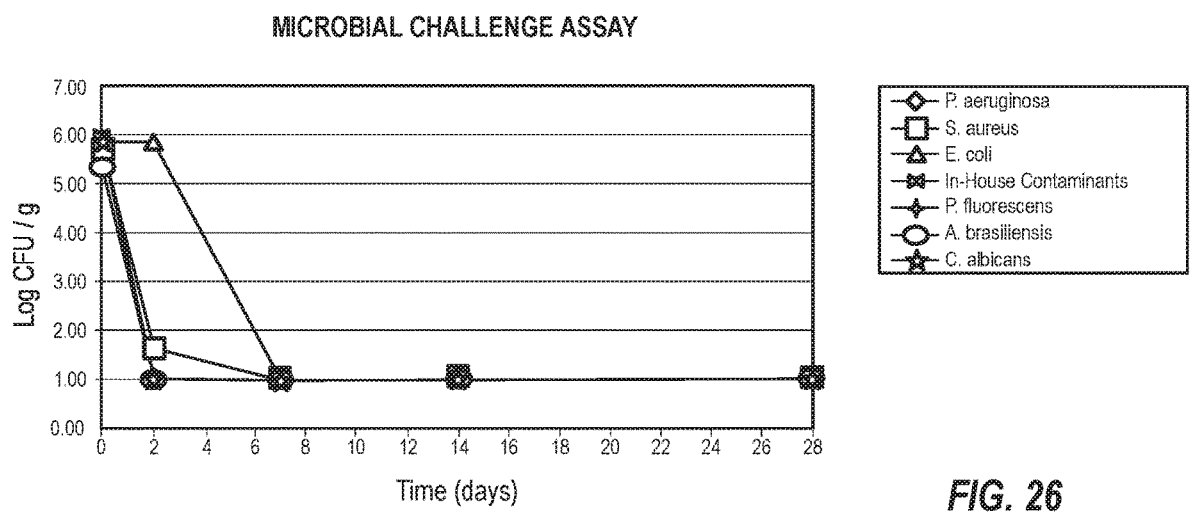
FIG. 26 illustrates the results of a microbial challenge assay using a modified version of the preservative system of FIG. 10 incorporated into an exemplary day cream composition in accordance with one embodiment of the disclosure.

A graphical representation of the results of microbial challenge assays performed for the exemplary preservative system of Example 26 is illustrated in FIG. 26—the preservative system being incorporated into a day cream moisturizer product, similar to FIG. 19-25.

As seen from the results illustrated in FIG. 26, the populations of all contaminants were completely reduced, with the populations of *C. albicans, A. brasiliensis, P. fluorescens*, In-House Contaminants, and *P. aeruginosa* completely reduced by day 2, with the populations of *S. aureus* and *E. coli* completely reduced by day 7.

The preservative system of Example 26 (i.e., including final concentrations of 4% *Lactobacillus* ferment, 4% *Lactobacillus* ferment & *Cocos nucifera* (Coconut) fruit extract, 0.2% salicylic acid, 0.4% potassium sorbate, and 4% propanediol within a suitable pH range according to embodiments of the present disclosure) can provide effective broad-spectrum protection in a cosmetic composition against microbial spoilage while using only natural ingredients and while also excluding phenoxyethanol, parabens, and formaldehyde donors which are universally applied in existing cosmetic preparations. In particular, the data from Example 26 illustrate that a lower concentration of salicylic acid (e.g., at least as low as 0.2%) is effective at providing broad-spectrum protection in combination with the other ingredients of the exemplary preservative formulation.

Example 27

Today, the seemingly never-ending launch of new skin care products making compelling performance claims, by both established and indie brands, pose a dilemma for consumers, namely, how to determine what/who to believe. At the end of the day, it all boils down to testing. For example, claims such as "look 10 years younger" or "reduce the appearance of fine lines and wrinkles by 50%" can certainly cause consumers to purchase these products with the expectation that they will do what they promise/claim. For those individuals inclined to believe the hype, it's instructive for them to read the fine print. There is oftentimes an asterisk adjacent to such claims that indicate that these performance claims are based on "in-vitro" testing results. In the real world, there is a significant difference between "in-vitro" testing versus "in-vivo" testing.

The term "in-vitro" is Latin for "in glass" which means the product is tested on a glass substrate (e.g. glass dish) that is certainly NOT the equivalent of human skin. When a product is evaluated using in-vitro testing, the product is evaluated in a lab using skin cells cultured in a glass dish that represent the outermost layer of a person's skin. The main problem with in-vitro testing to assess a product's efficacy is that one cannot determine whether the product's active ingredients will effectively penetrate the outermost layer of a user's skin (epidermis/stratum corneum) and reach the layer where the magic really happens, the dermis. Penetrating skin cells cultured on a glass surface is completely different from penetrating "actual" human skin.

One example of the deficiencies associated with in-vitro testing relates to a family of active ingredients found in wildly popular skin care products known as peptides. In the lab, i.e., on cells cultured in a glass dish, peptides have been shown to boost collagen production, reverse skin damage, lighten discoloration and make the cells look years younger. Unfortunately, these results are more often than not reproducible on actual human skin because most peptide molecules are too large to penetrate the outer layer (epidermis/stratum corneum) of a person's skin, meaning, they cannot possibly deliver the real-life performance properties their in-lab testing would suggest.

"In-vivo" testing, on the other hand, involves application of a product onto animal and/or human skin in order to assess its true efficacy. However, since animal testing is prohibited in Europe, and frowned upon in most other developed countries, testing on live human subjects is the most accurate and transparent method of assessing a product's efficacy.

Prior to utilizing in-vivo efficacy testing, however, it must first be determined that application of the product onto the skin of human volunteers will not cause them to experience an allergic reaction or some form of painful irritation. This is done by performing what is known as a Human Repeat Insult Patch Test (HRIPT). This is an internationally recognized test used to determine the potential for irritation, sensitization, and allergic reaction potential of a product. In view of the growing number of exotic ingredients used in skin care formulations, coupled with the increasingly complex and sophisticated chemical composition of the formulas, the risk of individuals experiencing irritation and allergic reactions because of their use has increased substantially. HRIPT is a skin patch test whereby patches containing the test product are applied multiple times onto the back of test subjects over a period of 6 weeks. This repeated contact with a potential allergen in the formula, if present, will generate a series of immunological reactions at the patch application site. Any allergic reactions experienced by the test subject will be observed, recorded, and evaluated by a dermatologist to confirm, or not, the safety of the product. Once a product is cleared from an HRIPT safety/toxicology perspective, it can then be used for in-vivo efficacy evaluation.

Embodiments of the disclosed preservative systems were incorporated into various topical consumer products and an HRIPT was performed to determine skin irritation and skin sensitization (e.g., contact allergy), if any, associated therewith.

Each HRIPT included about 50 subjects. In addition to demographic data collected for each subject, a Fitzpatrick Skin Type was also determined.

Materials and Methods for HRIPT Studies

Test materials to be tested under occlusive conditions were placed on an 8 mm aluminum Finn Chamber® (Epitest Ltd. Oy, Tuusula, Finland) supported on Scanpor® Tape (Norgesplaster A/S, Kristiansand, Norway) or an 8 mm filter paper coated aluminum Finn Chamber® AQUA supported on a thin flexible transparent polyurethane rectangular film coated on one side with a medical grade acrylic adhesive, consistent with adhesive used in state-of-the-art hypoallergenic surgical tapes or a 7 mm IQ-ULTRA® closed cell system which is made of additive-free polyethylene plastic foam with a filter paper incorporated (e.g., supplied in units of 10 chambers on a hypoallergenic non-woven adhesive tape; the width of the tape is 52 mm and the length is 118 mm) or other equivalents.

Test materials to be tested under semi-occlusive conditions were placed on a test strip with a Rayon/Polypropylene pad or on a 7.5 mm filter paper disc affixed to a strip of hypoallergenic tape (Johnson & Johnson 1-inch First Aid Cloth Tape).

Test materials to be tested in an open patch were applied and rubbed directly onto the back of the subject.

Approximately 0.02-0.05 mL (in case of liquids) and/or 0.02-0.05 g (in case of solids) of the test material was used for the study. Liquid test material was dispensed on a 7.5 mm paper disk that fit in the Finn Chamber.

Subjects were requested to bathe or wash as usual before arrival at the facility. Patches containing the test material were then affixed directly to the skin of the intrascapular regions of the back, to the right or left of the midline and subjects were dismissed with instructions not to wet or expose the test area to direct sunlight. Patches remained in place for 48 hours after the first application. Subjects were instructed not to remove the patches prior to their 48-hour scheduled visit. Thereafter, subjects were instructed to remove patches 24 hours after application for the remainder of the study.

This procedure was repeated until a series of 9 consecutive, 24-hour exposures had been made 3 times a week for three 3 consecutive weeks. Prior to each reapplication, the test sites evaluated by trained laboratory personnel. Following a 10-14-day rest period a retest/challenge dose was applied once to a previously unexposed test site, and test sites were evaluated by trained laboratory personnel 48 and 96 hours after application.

In the event of an adverse reaction, the area of erythema and edema would be measured. Edema is estimated by the evaluation of the skin with respect to the contour of the unaffected normal skin. Subjects were instructed to report any delayed reactions that might occur after the final reading.

Scoring scale and definition of symbols shown below are based on the scoring scheme according to the International Contact Dermatitis Research Group scoring scale listed in Table 7 below:

TABLE 7

| Scoring Scale | Definition |
|---|---|
| 0 | No reaction (negative) |
| 1 | Erythema throughout at least ¾ of patch area |
| 2 | Erythema and induration throughout at least ¾ of patch area |
| 3 | Erythema, induration, and vesicles |
| 4 | Erythema, induration, and bullae |
| D | Site discontinued |
| Dc | Subject discontinued voluntarily |
| Dcl | Subject discontinued per investigator |

Clinical evaluations were performed by an investigator or designee trained in the clinical evaluation of the skin. When feasible, the same individual scored all the subjects throughout the study and was blinded to the treatment assignments and any previous scores.

In Example 27, an eye gel containing an all-natural preservative system disclosed herein (having at least 0.45% salicylic acid) was evaluated in an HRIPT study, according to the methods described above. The demographic data and Fitzpatrick Skin Type for each of the 58 subjects completing the study are provided in Table 8 below.

TABLE 8

| HRIPT re Eye Gel | |
|---|---|
| # subjects enrolled | 61 |
| # subjects completing study | 58 |
| Age range | 19-65 |
| Sex | |
| Male | 8 |
| Female | 50 |
| Fitzpatrick Skin Type | |
| 1-always burn, does not tan | 0 |
| 2-burn easily, tan slightly | 15 |
| 3-burn moderately, tan progressively | 16 |
| 4-burn a little, always tan | 9 |
| 5-rarely burn, tan intensely | 18 |
| 6-never burn, tan very intensely | 0 |

The results of the HRIPT study with respect to the eye gel having a preservative system disclosed herein (including at least 0.45% salicylic acid) are provided in Table 9 below. During the study of Example 27, an occlusive patch was used.

TABLE 9

| Subject | Skin Type | Induction | | | | | | | | | Challenge | |
|---|---|---|---|---|---|---|---|---|---|---|---|---|
| | | 1 | 2 | 3 | 4 | 5 | 6 | 7 | 8 | 9 | 1 | 2 |
| 1 | 3 | 0 | 0 | 0 | 0 | 0 | 0 | 0 | 0 | 0 | 0 | 0 |
| 2 | 5 | 0 | 0 | 0 | 0 | 0 | 0 | 0 | 0 | 0 | Dc | Dc |
| 3 | 2 | 0 | 0 | 0 | 0 | 0 | 0 | 0 | 0 | 0 | 0 | 0 |
| 4 | 2 | 0 | 0 | 0 | 0 | 0 | 0 | 0 | 0 | 0 | 0 | 0 |
| 5 | 2 | 0 | 0 | 0 | 0 | 0 | 0 | 0 | 0 | 0 | 0 | 0 |
| 6 | 4 | 0 | 0 | 0 | 0 | 0 | 0 | 0 | 0 | 0 | 0 | 0 |
| 7 | 5 | 0 | 0 | 0 | 0 | 0 | 0 | 0 | 0 | 0 | 0 | 0 |
| 8 | 5 | 0 | 0 | 0 | 0 | 0 | 0 | 0 | 0 | 0 | 0 | 0 |
| 9 | 3 | 0 | 0 | 0 | 0 | 0 | 0 | 0 | 0 | 0 | 0 | 0 |
| 10 | 2 | 0 | 0 | 0 | 0 | 0 | 0 | 0 | 0 | 0 | 0 | 0 |
| 11 | 5 | 0 | 0 | 0 | 0 | 0 | 0 | 0 | 0 | 0 | 0 | 0 |
| 12 | 2 | 0 | 0 | 0 | 0 | 0 | 0 | 0 | 0 | 0 | 0 | 0 |
| 13 | 3 | 0 | 0 | 0 | 0 | 0 | 0 | 0 | 0 | 0 | 0 | 0 |
| 14 | 2 | 0 | 0 | 0 | 0 | 0 | 0 | 0 | 0 | 0 | 0 | 0 |
| 15 | 5 | 0 | 0 | 0 | 0 | 0 | 0 | 0 | 0 | 0 | 0 | 0 |
| 16 | 4 | 0 | 0 | 0 | 0 | 0 | 0 | 0 | 0 | 0 | 0 | 0 |
| 17 | 3 | 0 | 0 | 0 | 0 | 0 | 0 | 0 | 0 | 0 | 0 | 0 |
| 18 | 4 | 0 | 0 | 0 | 0 | 0 | 0 | 0 | 0 | 0 | 0 | 0 |
| 19 | 5 | 0 | 0 | 0 | 0 | 0 | 0 | 0 | 0 | 0 | 0 | 0 |
| 20 | 5 | 0 | 0 | 0 | 0 | 0 | 0 | 0 | 0 | 0 | 0 | 0 |
| 21 | 2 | 0 | 0 | 0 | 0 | 0 | 0 | 0 | 0 | 0 | 0 | 0 |
| 22 | 2 | 0 | 0 | 0 | 0 | 0 | 0 | 0 | 0 | 0 | 0 | 0 |
| 23 | 4 | 0 | 0 | 0 | 0 | 0 | 0 | 0 | 0 | 0 | 0 | 0 |
| 24 | 3 | 0 | 0 | 0 | 0 | 0 | 0 | 0 | 0 | 0 | 0 | 0 |
| 25 | 3 | 0 | 0 | 0 | 0 | 0 | 0 | 0 | 0 | 0 | 0 | 0 |
| 26 | 3 | 0 | 0 | 0 | 0 | 0 | 0 | 0 | 0 | 0 | 0 | 0 |
| 27 | 5 | 0 | 0 | 0 | 0 | 0 | 0 | 0 | 0 | 0 | 0 | 0 |
| 28 | 4 | 0 | 0 | 0 | 0 | 0 | 0 | 0 | 0 | 0 | 0 | 0 |
| 29 | 2 | 0 | 0 | Dc | Dc | Dc | Dc | Dc | Dc | Dc | Dc | Dc |
| 30 | 5 | 0 | 0 | 0 | 0 | 0 | 0 | 0 | 0 | 0 | 0 | 0 |
| 31 | 5 | 0 | 0 | 0 | 0 | 0 | 0 | 0 | 0 | 0 | 0 | 0 |
| 32 | 3 | 0 | 0 | 0 | 0 | 0 | 0 | 0 | 0 | 0 | 0 | 0 |
| 33 | 4 | 0 | 0 | 0 | 0 | 0 | 0 | 0 | 0 | 0 | 0 | 0 |
| 34 | 5 | 0 | 0 | 0 | 0 | 0 | 0 | 0 | 0 | 0 | 0 | 0 |
| 35 | 2 | 0 | 0 | 0 | 0 | 0 | 0 | 0 | 0 | Dc | Dc | Dc |
| 36 | 5 | 0 | 0 | 0 | 0 | 0 | 0 | 0 | 0 | 0 | 0 | 0 |
| 37 | 5 | 0 | 0 | 0 | 0 | 0 | 0 | 0 | 0 | 0 | 0 | 0 |
| 38 | 2 | 0 | 0 | 0 | 0 | 0 | 0 | 0 | 0 | 0 | 0 | 0 |
| 39 | 2 | 0 | 0 | 0 | 0 | 0 | 0 | 0 | 0 | 0 | 0 | 0 |
| 40 | 4 | 0 | 0 | 0 | 0 | 0 | 0 | 0 | 0 | 0 | 0 | 0 |
| 41 | 3 | 0 | 0 | 0 | 0 | 0 | 0 | 0 | 0 | 0 | 0 | 0 |
| 42 | 2 | 0 | 0 | 0 | 0 | 0 | 0 | 0 | 0 | 0 | 0 | 0 |
| 43 | 5 | 0 | 0 | 0 | 0 | 0 | 0 | 0 | 0 | 0 | 0 | 0 |
| 44 | 3 | 0 | 0 | 0 | 0 | 0 | 0 | 0 | 0 | 0 | 0 | 0 |
| 45 | 4 | 0 | 0 | 0 | 0 | 0 | 0 | 0 | 0 | 0 | 0 | 0 |
| 46 | 2 | 0 | 0 | 0 | 0 | 0 | 0 | 0 | 0 | 0 | 0 | 0 |
| 47 | 3 | 0 | 0 | 0 | 0 | 0 | 0 | 0 | 0 | 0 | 0 | 0 |
| 48 | 3 | 0 | 0 | 0 | 0 | 0 | 0 | 0 | 0 | 0 | 0 | 0 |
| 49 | 2 | 0 | 0 | 0 | 0 | 0 | 0 | 0 | 0 | 0 | 0 | 0 |
| 50 | 5 | 0 | 0 | 0 | 0 | 0 | 0 | 0 | 0 | 0 | 0 | 0 |

TABLE 9-continued

| Sub-ject | Skin Type | Induction | | | | | | | | | Challenge | |
|---|---|---|---|---|---|---|---|---|---|---|---|---|
| | | 1 | 2 | 3 | 4 | 5 | 6 | 7 | 8 | 9 | 1 | 2 |
| 51 | 3 | 0 | 0 | 0 | 0 | 0 | 0 | 0 | 0 | 0 | 0 | 0 |
| 52 | 5 | 0 | 0 | 0 | 0 | 0 | 0 | 0 | 0 | 0 | 0 | 0 |
| 53 | 2 | 0 | 0 | 0 | 0 | 0 | 0 | 0 | 0 | 0 | 0 | 0 |
| 54 | 4 | 0 | 0 | 0 | 0 | 0 | 0 | 0 | 0 | 0 | 0 | 0 |
| 55 | 3 | 0 | 0 | 0 | 0 | 0 | 0 | 0 | 0 | 0 | 0 | 0 |
| 56 | 3 | 0 | 0 | 0 | 0 | 0 | 0 | 0 | 0 | 0 | 0 | 0 |
| 57 | 5 | 0 | 0 | 0 | 0 | 0 | 0 | 0 | 0 | 0 | 0 | 0 |
| 58 | 5 | 0 | 0 | 0 | 0 | 0 | 0 | 0 | 0 | 0 | 0 | 0 |
| 59 | 5 | 0 | 0 | 0 | 0 | 0 | 0 | 0 | 0 | 0 | 0 | 0 |
| 60 | 2 | 0 | 0 | 0 | 0 | 0 | 0 | 0 | 0 | 0 | 0 | 0 |
| 61 | 3 | 0 | 0 | 0 | 0 | 0 | 0 | 0 | 0 | 0 | 0 | 0 |

As is evident from the results displayed in Table 9, there was no indication of a potential to elicit dermal irritation or sensitization (contact allergy) for the eye gel. Each subject completing the study never presented with a score over a 0 during induction or challenge.

Example 28

In Example 28, a day cream containing an all-natural preservative system disclosed herein (having at least 0.45% salicylic acid) was evaluated in an HRIPT study, according to the methods described above. The demographic data and Fitzpatrick Skin Type for each of the 51 subjects completing the study are provided in Table 10 below.

TABLE 10

HRIPT re Day Cream

| | |
|---|---|
| # subjects enrolled | 55 |
| # subjects completing study | 51 |
| Age range | 19-53 |
| Sex | |
| Male | 5 |
| Female | 46 |
| Fitzpatrick Skin Type | |
| 1-always burn, does not tan | 0 |
| 2-burn easily, tan slightly | 0 |
| 3-burn moderately, tan progressively | 51 |
| 4-burn a little, always tan | 0 |
| 5-rarely burn, tan intensely | 0 |
| 6-never burn, tan very intensely | 0 |

The results of the HRIPT study with respect to the day cream having a preservative system disclosed herein (including at least 0.45% salicylic acid) are provided in Table 11 below. During the study of Example 28, a semi-occlusive patch was used.

TABLE 11

| Sub-ject | Skin Type | Induction | | | | | | | | | Challenge | |
|---|---|---|---|---|---|---|---|---|---|---|---|---|
| | | 1 | 2 | 3 | 4 | 5 | 6 | 7 | 8 | 9 | 1 | 2 |
| 1 | 3 | 0 | 0 | 0 | 0 | 0 | 0 | 0 | 0 | 0 | 0 | 0 |
| 2 | 3 | 0 | 0 | 0 | 0 | 0 | 0 | 0 | 0 | 0 | 0 | 0 |
| 3 | 3 | 0 | 0 | 0 | 0 | 0 | 0 | 0 | 0 | 0 | 0 | 0 |
| 4 | 3 | 0 | 0 | 0 | 0 | 0 | 0 | 0 | 0 | 0 | 0 | 0 |
| 5 | 3 | 0 | 0 | 0 | 0 | 0 | 0 | 0 | 0 | 0 | 0 | 0 |
| 6 | 3 | 0 | 0 | Dc | Dc | Dc | Dc | Dc | Dc | Dc | Dc | Dc |
| 7 | 3 | 0 | 0 | 0 | 0 | 0 | 0 | Dc | Dc | Dc | Dc | Dc |
| 8 | 3 | 0 | 0 | 0 | 0 | 0 | 0 | 0 | 0 | 0 | 0 | 0 |
| 9 | 3 | 0 | 0 | Dc | Dc | Dc | Dc | Dc | Dc | Dc | Dc | Dc |
| 10 | 3 | 0 | 0 | 0 | 0 | 0 | 0 | 0 | 0 | 0 | 0 | 0 |

TABLE 11-continued

| Sub-ject | Skin Type | Induction | | | | | | | | | Challenge | |
|---|---|---|---|---|---|---|---|---|---|---|---|---|
| | | 1 | 2 | 3 | 4 | 5 | 6 | 7 | 8 | 9 | 1 | 2 |
| 11 | 3 | 0 | 0 | 0 | 0 | 0 | 0 | 0 | 0 | 0 | 0 | 0 |
| 12 | 3 | 0 | 0 | 0 | 0 | 0 | 0 | 0 | 0 | 0 | Dc | Dc |
| 13 | 3 | 0 | 0 | 0 | 0 | 0 | 0 | 0 | 0 | 0 | 0 | 0 |
| 14 | 3 | 0 | 0 | 0 | 0 | 0 | 0 | 0 | 0 | 0 | 0 | 0 |
| 15 | 3 | 0 | 0 | 0 | 0 | 0 | 0 | 0 | 0 | 0 | 0 | 0 |
| 16 | 3 | 0 | 0 | 0 | 0 | 0 | 0 | 0 | 0 | 0 | 0 | 0 |
| 17 | 3 | 0 | 0 | 0 | 0 | 0 | 0 | 0 | 0 | 0 | 0 | 0 |
| 18 | 3 | 0 | 0 | 0 | 0 | 0 | 0 | 0 | 0 | 0 | 0 | 0 |
| 19 | 3 | 0 | 0 | 0 | 0 | 0 | 0 | 0 | 0 | 0 | 0 | 0 |
| 20 | 3 | 0 | 0 | 0 | 0 | 0 | 0 | 0 | 0 | 0 | 0 | 0 |
| 21 | 3 | 0 | 0 | 0 | 0 | 0 | 0 | 0 | 0 | 0 | 0 | 0 |
| 22 | 3 | 0 | 0 | 0 | 0 | 0 | 0 | 0 | 0 | 0 | 0 | 0 |
| 23 | 3 | 0 | 0 | 0 | 0 | 0 | 0 | 0 | 0 | 0 | 0 | 0 |
| 24 | 3 | 0 | 0 | 0 | 0 | 0 | 0 | 0 | 0 | 0 | 0 | 0 |
| 25 | 3 | 0 | 0 | 0 | 0 | 0 | 0 | 0 | 0 | 0 | 0 | 0 |
| 26 | 3 | 0 | 0 | 0 | 0 | 0 | 0 | 0 | 0 | 0 | 0 | 0 |
| 27 | 3 | 0 | 0 | 0 | 0 | 0 | 0 | 0 | 0 | 0 | 0 | 0 |
| 28 | 3 | 0 | 0 | 0 | 0 | 0 | 0 | 0 | 0 | 0 | 0 | 0 |
| 29 | 3 | 0 | 0 | 0 | 0 | 0 | 0 | 0 | 0 | 0 | 0 | 0 |
| 30 | 3 | 0 | 0 | 0 | 0 | 0 | 0 | 0 | 0 | 0 | 0 | 0 |
| 31 | 3 | 0 | 0 | 0 | 0 | 0 | 0 | 0 | 0 | 0 | 0 | 0 |
| 32 | 3 | 0 | 0 | 0 | 0 | 0 | 0 | 0 | 0 | 0 | 0 | 0 |
| 33 | 3 | 0 | 0 | 0 | 0 | 0 | 0 | 0 | 0 | 0 | 0 | 0 |
| 34 | 3 | 0 | 0 | 0 | 0 | 0 | 0 | 0 | 0 | 0 | 0 | 0 |
| 35 | 3 | 0 | 0 | 0 | 0 | 0 | 0 | 0 | 0 | 0 | 0 | 0 |
| 36 | 3 | 0 | 0 | 0 | 0 | 0 | 0 | 0 | 0 | 0 | 0 | 0 |
| 37 | 3 | 0 | 0 | 0 | 0 | 0 | 0 | 0 | 0 | 0 | 0 | 0 |
| 38 | 3 | 0 | 0 | 0 | 0 | 0 | 0 | 0 | 0 | 0 | 0 | 0 |
| 40 | 3 | 0 | 0 | 0 | 0 | 0 | 0 | 0 | 0 | 0 | 0 | 0 |
| 41 | 3 | 0 | 0 | 0 | 0 | 0 | 0 | 0 | 0 | 0 | 0 | 0 |
| 42 | 3 | 0 | 0 | 0 | 0 | 0 | 0 | 0 | 0 | 0 | 0 | 0 |
| 43 | 3 | 0 | 0 | 0 | 0 | 0 | 0 | 0 | 0 | 0 | 0 | 0 |
| 44 | 3 | 0 | 0 | 0 | 0 | 0 | 0 | 0 | 0 | 0 | 0 | 0 |
| 45 | 3 | 0 | 0 | 0 | 0 | 0 | 0 | 0 | 0 | 0 | 0 | 0 |
| 46 | 3 | 0 | 0 | 0 | 0 | 0 | 0 | 0 | 0 | 0 | 0 | 0 |
| 47 | 3 | 0 | 0 | 0 | 0 | 0 | 0 | 0 | 0 | 0 | 0 | 0 |
| 48 | 3 | 0 | 0 | 0 | 0 | 0 | 0 | 0 | 0 | 0 | 0 | 0 |
| 49 | 3 | 0 | 0 | 0 | 0 | 0 | 0 | 0 | 0 | 0 | 0 | 0 |
| 50 | 3 | 0 | 0 | 0 | 0 | 0 | 0 | 0 | 0 | 0 | 0 | 0 |
| 51 | 3 | 0 | 0 | 0 | 0 | 0 | 0 | 0 | 0 | 0 | 0 | 0 |

As is evident from the results displayed in Table 11, there was no indication of a potential to elicit dermal irritation or sensitization (contact allergy) for the day cream.

Each subject completing the study never presented with a score over a 0 during induction or challenge. Accordingly, there were no adverse reactions of any kind reported during the course of the study. There were one subject with a Grade 3 reaction and 4 subjects with a Grade 1 reaction to the positive control (2.0% Sodium Lauryl Sulfate Solution), and no subjects showed any signs of reaction to the negative control (DI water).

Examples 29-32

The same cohort of subjects of Example 28 (i.e., whose demographics are described in Table 10 above) were used in HRIPT studies for an exfoliating wash containing an all-natural preservative system disclosed herein but without any salicylic acid added (Example 29), an exfoliating wash containing an all-natural preservative system disclosed herein with at least 0.45% salicylic acid (Example 30), a skin moisturizer containing an all-natural preservative system disclosed herein but without any salicylic acid added (Example 31), and a skin moisturizer containing an all-natural preservative system disclosed herein with at least 0.45% salicylic acid (Example 32).

The results of the HRIPT studies for Examples 29-32 are identical to those disclosed in Table 11. That is, there was no indication of a potential to elicit dermal irritation or sensitization (contact allergy) for any of the topical consumer products of Examples 29-32. During the studies of Examples 29-32, a semi-occlusive patch was used.

Examples 27-32 illustrate the gentle, non-irritating or sensitizing nature of the disclosed preservative systems and additional unexpected benefits to their use and incorporation into topical consumer products.

By providing a preservative system according to embodiments of the disclosure, the problem of existing preservative systems using harsh, synthetic, petroleum-based, and/or harmful ingredients is addressed while maintaining effective broad-spectrum protection against and inhibition of microbial growth in a cosmetic formulation. The embodiments of the disclosure advantageously maintain broad-spectrum protection without the use of phenoxyethanol, parabens, or formaldehyde donors, and comprise natural ingredients in specific, targeted amounts that further avoid any deleterious skin-irritation effects.

While the disclosure discusses embodiments of a preservative system for certain compositions including cosmetic formulations, preservative systems according to embodiments of the disclosure may be used with other types of compositions and for alternative uses.

Not necessarily all such objects or advantages may be achieved under any embodiment of the disclosure. Those skilled in the art will recognize that the disclosure may be embodied or carried out to achieve or optimize one advantage or group of advantages as taught without achieving other objects or advantages as taught or suggested.

The skilled artisan will recognize the interchangeability of various components of different embodiments described. Besides the variations described, other known equivalents for each feature can be mixed and matched by one of ordinary skill in this art to arrive at a preservative system under principles of the present disclosure. Therefore, the embodiments described may be adapted to preservative systems for other types of compositions and for other uses than those described and having other components than those described.

Although a preservative system has been disclosed in certain preferred embodiments and examples, it nevertheless will be understood by those skilled in the art that the present disclosure extends beyond the disclosed embodiments to other alternative embodiments and/or uses of the disclosure and obvious modifications and equivalents. It is intended that the scope of the present disclosure should not be limited by the disclosed embodiments described above but should be determined only by a fair reading of the claims that follow.

What is claimed is:

1. A composition intended for application onto human skin, hair, and/or nails comprising an antimicrobial effective amount of a preservative system comprising:
   (a) from about 1 to about 5% by weight of a *Lactobacillus* ferment;
   (b) from about 1 to about 5% by weight of a *Cocos nucifera* fruit extract fermented with *Lactobacillus*;
   (c) up to about 0.5% by weight of at least one co-preservative ingredient chosen from salicylic acid or a salt of a weak acid; and
   (d) from about 1 to about 10% by weight of a petroleum-free propanediol,
   wherein all weights are based on a total weight of the composition, and
   wherein the composition has a pH ranging from about 4.5 to about 5.5.

2. The composition of claim 1, wherein the at least one co-preservative ingredient is salicylic acid employed in an amount from about 0.2 to about 0.45% by weight, based on the total weight of the composition.

3. The composition of claim 1, wherein the at least one co-preservative ingredient is a salt of a weak acid employed in an amount of from about 0.2 to about 0.4% by weight, based on the total weight of the composition.

4. The composition of claim 3, wherein the salt of a weak acid is potassium sorbate.

5. The composition of claim 1, wherein the at least one co-preservative ingredient is a mixture of from about 0.2 to about 0.45% by weight of salicylic acid and from about 0.2 to about 0.4% by weight of potassium sorbate, all weights based on the total weight of the composition.

6. The composition of claim 1, wherein (d) is employed in an amount of from about 2 to about 8% by weight, based on the total weight of the composition.

7. The composition of claim 1, wherein (d) is employed in an amount of from about 4 to about 6% by weight, based on the total weight of the composition.

8. The composition of claim 1, wherein the composition is natural, organic, ECOCERT®-approved, and free of petroleum-derived ingredients.

9. The composition of claim 1, wherein the composition is free of any primary antimicrobial agents chosen from parabens, phenoxyethanol, formaldehyde donors, and combinations thereof.

10. The composition of claim 1, wherein the composition comprises a skin topic comprising one or more of a cream, lotion, serum, mist, spray, or wash.

11. The composition of claim 1, wherein the composition is intended for use on keratinous substances, including human hair and nails, the composition comprising one or more of mascara, shampoo, nail polish, or conditioner.

12. The composition of claim 1, wherein the preservative system additionally comprises from about 0.2 to about 0.4% by weight of potassium sorbate,
   wherein (a) is employed in an amount from about 2 to about 4% by weight,
   wherein (b) is employed in an amount from about 2 to about 4% by weight,
   wherein (c) is employed from about 0.2 to about 0.45% by weight,
   wherein (d) is employed from about 4 to about 6% by weight, and
   wherein the composition has a pH ranging from about 4.8 to about 5.3.

13. The composition of claim 12, wherein the composition is natural, organic, ECOCERT®-approved, and free of petroleum-derived ingredients.

14. The composition of claim 12, wherein the composition is free of any primary antimicrobial agents chosen from parabens, phenoxyethanol, formaldehyde donors, and combinations thereof.

15. A method of preventing and inhibiting microbial growth on or in a composition intended for application onto human skin, comprising:
   adding to the composition an antimicrobial effective amount of a preservative system containing:
   (a) from about 2 to about 5% by weight of a *Lactobacillus* ferment;
   (b) from about 2 to about 5% by weight of a *Cocos nucifera* fruit extract fermented with *Lactobacillus*;
   (c) from about 0.1 to about 0.5% by weight of at least one co-preservative ingredient chosen from salicylic acid and a salt of a weak acid; and (d) from about 1 to about 10% by weight of a petroleum-free propanediol, wherein all weights are based on a total weight of the composition, and wherein the composition has a pH ranging from about 4.5 to about 5.5.

16. The method of claim 15, wherein the at least one co-preservative ingredient is one or more of salicylic acid provided in an amount of from about 0.2 to about 0.45% by weight or potassium sorbate provided in an amount of from about 0.2 to about 0.4% by weight, based on the total weight of the composition.

17. The method of claim 16, wherein (d) is provided in an amount of from about 4 to about 6% by weight, based on the total weight of the composition.

18. A preservative system, comprising:
(a) from about 2 to about 8% by weight of a *Lactobacillus* ferment;
(b) from about 2 to about 4% by weight of a *Cocos nucifera* fruit extract fermented with *Lactobacillus*;
(c) from about 0.2 to about 0.4% by weight of potassium sorbate; and
(d) from about 4 to about 6% by weight of a petroleum-free propanediol,
wherein all weights are based on a total weight of a composition into which the preservative system is applied, and
wherein the composition has a pH ranging from about 4.5 to about 5.5.

19. The preservative system of claim 18, further comprising from about 0.2 to about 0.45% by weight of salicylic acid.

20. The preservative system of claim 19, wherein the composition has a pH ranging from about 4.8 to about 5.3.

21. The preservative system of claim 18, wherein the preservative system comprises:
(a) about 4% by weight of the *Lactobacillus* ferment;
(b) about 4% by weight of the *Lactobacillus* and *Cocos nucifera* fruit extract;
(c) about 0.2% by weight of the potassium sorbate; and
(d) about 4% by weight of the petroleum-free propanediol.

22. The preservative system of claim 18, wherein the preservative system comprises:
(a) about 4% by weight of the *Lactobacillus* ferment;
(b) about 4% by weight of the *Lactobacillus* and *Cocos nucifera* fruit extract;
(c) about 0.4% by weight of the potassium sorbate; and
(d) about 4% by weight of the petroleum-free propanediol.

* * * * *